US012616442B2

(12) United States Patent
Cohen et al.

(10) Patent No.: US 12,616,442 B2
(45) Date of Patent: May 5, 2026

(54) SYSTEMS, DEVICES, AND METHODS FOR COREGISTRATION OF INTRAVASCULAR DATA TO ENHANCED STENT DEPLOYMENT X-RAY IMAGES

(71) Applicant: PHILIPS IMAGE GUIDED THERAPY CORPORATION, San Diego, CA (US)

(72) Inventors: Asher Cohen, San Diego, CA (US); Pei-Yin Chao, Eindhoven (NL); Ronald Christiaan Helmstrijd, Eindhoven (NL); Ehud Nachtomy, Herzliya (IL)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 328 days.

(21) Appl. No.: 18/082,405

(22) Filed: Dec. 15, 2022

(65) Prior Publication Data

US 2023/0190228 A1    Jun. 22, 2023

Related U.S. Application Data

(60) Provisional application No. 63/331,299, filed on Apr. 15, 2022, provisional application No. 63/290,694, filed on Dec. 17, 2021.

(51) Int. Cl.
*A61B 8/12*        (2006.01)
*A61B 8/08*        (2006.01)
*A61B 8/00*        (2006.01)

(52) U.S. Cl.
CPC .............. *A61B 8/12* (2013.01); *A61B 8/0891* (2013.01); *A61B 8/463* (2013.01)

(58) Field of Classification Search
CPC ......... A61B 8/12; A61B 8/0891; A61B 8/463; A61B 6/481; A61B 6/487; A61B 6/12; A61B 6/4417; A61B 6/463; A61B 8/4416
See application file for complete search history.

(56) References Cited

U.S. PATENT DOCUMENTS 6,200,268 B1    3/2001   Vince
6,381,350 B1    4/2002   Klingensmith
            (Continued)

FOREIGN PATENT DOCUMENTS

DE        102007023719 A      5/2007

*Primary Examiner* — Bo Joseph Peng

(57)        ABSTRACT

A system includes a processor circuit in communication with an extraluminal imaging device and an intraluminal imaging device. The processor circuit obtains an enhanced stent deployment extraluminal image and a plurality of intraluminal images. The enhanced stent deployment extraluminal image and the each of the plurality of intraluminal images are associated with locations along a pathway. The pathway is overlaid over an extraluminal image. Based on the locations of the pathway, the processor circuit coregisters the plurality of intraluminal images to the enhanced stent deployment extraluminal image and outputs a screen display of one of the plurality of intraluminal images and the enhanced stent deployment extraluminal image with an indicator identifying the location at which the displayed intraluminal image was obtained. The processor circuit may also determine an expansion score for intraluminal images depicting the stent and identify regions of the stent corresponding to an expansions score below a threshold.

16 Claims, 12 Drawing Sheets

(56)  References Cited

U.S. PATENT DOCUMENTS

| | | | |
|---|---|---|---|
| 6,776,763 | B2 | 8/2004 | Nix |
| 7,074,188 | B2 | 7/2006 | Nair |
| 7,175,597 | B2 | 2/2007 | Vince |
| 7,215,802 | B2 | 5/2007 | Klingensmith |
| 7,226,417 | B1 | 6/2007 | Eberle |
| 7,359,554 | B2 | 4/2008 | Klingensmith |
| 7,463,759 | B2 | 12/2008 | Klingensmith |
| 7,846,101 | B2 | 12/2010 | Eberle |
| 7,930,014 | B2 | 4/2011 | Huennekens |
| 7,941,000 | B2 | 5/2011 | Rongen |
| 8,290,228 | B2 | 10/2012 | Cohen |
| 8,463,007 | B2 | 6/2013 | Steinberg |
| 8,670,603 | B2 | 3/2014 | Tolkowsky |
| 8,693,756 | B2 | 4/2014 | Tolkowsky |
| 8,781,193 | B2 | 7/2014 | Steinberg |
| 8,855,744 | B2 | 10/2014 | Tolkowsky |
| 10,076,301 | B2 | 9/2018 | Millett |
| 11,413,017 | B2 | 8/2022 | Stigall |
| 2010/0114289 | A1* | 5/2010 | Camus ...................... A61F 2/95<br>623/1.11 |
| 2015/0282737 | A1* | 10/2015 | Tolkowsky ............ A61B 5/066<br>600/424 |
| 2019/0282182 | A1 | 9/2019 | Scott |
| 2019/0282211 | A1 | 9/2019 | Merritt |
| 2019/0365480 | A1 | 12/2019 | Gopinath |
| 2020/0029861 | A1* | 1/2020 | Rajguru .................. A61B 8/12 |
| 2020/0029932 | A1 | 1/2020 | Cohen |
| 2020/0294659 | A1 | 9/2020 | Gopinath |
| 2023/0005135 | A1 | 1/2023 | Bydlon |

* cited by examiner

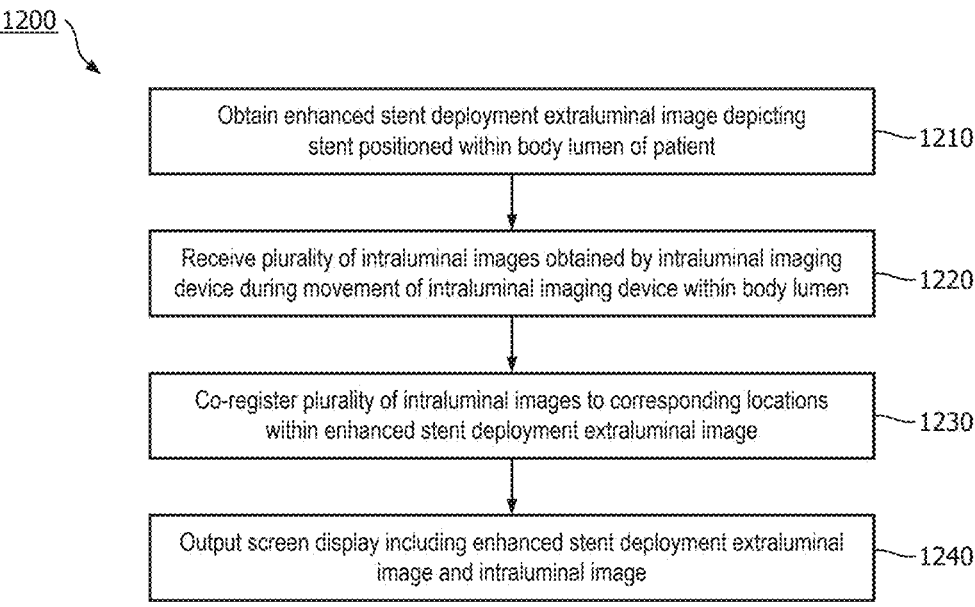

1200

Obtain enhanced stent deployment extraluminal image depicting stent positioned within body lumen of patient — 1210

Receive plurality of intraluminal images obtained by intraluminal imaging device during movement of intraluminal imaging device within body lumen — 1220

Co-register plurality of intraluminal images to corresponding locations within enhanced stent deployment extraluminal image — 1230

Output screen display including enhanced stent deployment extraluminal image and intraluminal image — 1240

FIG. 12

SYSTEMS, DEVICES, AND METHODS FOR COREGISTRATION OF INTRAVASCULAR DATA TO ENHANCED STENT DEPLOYMENT X-RAY IMAGES

CROSS-REFERENCE TO RELATED APPLICATIONS

This application claims priority to and the benefit of U.S. Provisional Application No. 63/290,694, filed Dec. 17, 2021 and U.S. Provisional Application No. 63/331,299, filed Apr. 15, 2022, each of which is incorporated by reference herein in its entirety.

TECHNICAL FIELD

The present disclosure relates generally to co-registering data from different medical diagnostic modalities. In particular, intravascular data may be co-registered to enhanced stent deployment x-ray images and used to assess the success of a stent deployment procedure.

BACKGROUND

Physicians use many different medical diagnostic systems and tools to monitor a patient's health and diagnose medical conditions. Different modalities of medical diagnostic systems may provide a physician with different images, models, and/or data relating to internal structures within a patient. These modalities include invasive devices and systems, such as intravascular systems, and non-invasive devices and systems, such as x-ray systems, and computed tomography (CT) systems. Using multiple diagnostic systems to examine a patient's anatomy provides a physician with added insight into the condition of the patient.

In the field of intravascular imaging, co-registration of data from invasive devices (e.g., intraluminal devices such as intravascular ultrasound (IVUS) devices or instantaneous wave-free ratio (iFR) devices) with images collected non-invasively (e.g., extraluminal images, such as those obtained via x-ray angiography) is a powerful technique for improving the efficiency and accuracy of vascular catheterization procedures. Co-registration identifies the locations of intravascular data measurements along a blood vessel by mapping the data to an angiography image of the vessel. A physician may then know exactly where in the vessel a measurement was made, rather than estimate the location.

During a treatment procedure, a stent may be positioned within a patient's vessel at a constriction of the vessel to restore blood flow. Incorrect placement or insufficient expansion of a stent may lead to a failure to restore blood flow as well as complications post deployment. The physician has been limited to a view of an extraluminal image, such as a stent-enhanced image, to assess whether a stent was correctly positioned and/or expanded within the vessel.

SUMMARY

Embodiments of the present disclosure are systems, devices, and methods for co-registering intravascular data to enhanced stent deployment x-ray images. Aspects of the present disclosure advantageously provide a physician with information regarding the success of a stent deployment procedure. Specifically, aspects of the present disclosure help a physician confirm whether a stent is properly expanded after deployment as well as determine whether the stent was placed at a correct location longitudinally along a vessel so that a central portion of the stent is placed at or near the constriction of the vessel. For example, the physician is no longer limited to the extraluminal image, such as the stent-enhanced image, alone. Rather, the physician is additionally able to use intravascular data (e.g., intraluminal images, such as IVUS image) that have been co-registered with the stent-enhanced image to evaluate correct positioning and/or expansion of the stent.

At a first step, a stent is positioned within a vessel while x-ray images of the vessel are acquired. The x-ray images are used to co-register the location of the stent, including the location of the stent after expansion, as well as to generate stent-enhanced images to enhance the view of the stent for the physician after stent expansion. Because radiopaque portions of the stent and/or delivery device are visible in the x-ray images, the location of the stent within the x-ray images is known throughout the procedure. After the stent is expanded, an intravascular ultrasound (IVUS) imaging device may be pulled through the vessel and the stent while x-ray images of the stented region are acquired. During the IVUS imaging procedure, because radiopaque portions of the imaging device appear within the x-ray images, the locations at which IVUS images were acquired may also be known. The locations of the stent and the locations of the intravascular imaging device are both coregistered to the same x-ray image. As a result, IVUS images, and any accompanying data, such as stent expansion scores, may be coregistered to the stent-enhanced images.

Aspects of the present disclosure include displaying a stent boosted image with superimposed IVUS data, such as stent expansion scores. The IVUS data may also be superimposed on a longitudinal view of the vessel. These displays advantageously provide a physician with information regarding whether the stent was correctly placed and sufficiently expanded to both restore blood flow and reduce the risk of further complications related to the stent. An advantage of the present disclosure may also include exploiting synergies among various medical systems and applications as well as reducing procedure time spent switching between varying systems and apps. The present disclosure may also assist a physician to interpret a stent-enhanced image and IVUS images.

In an exemplary aspect, a system is provided. The system includes a processor circuit configured for communication with an extraluminal imaging device and an intraluminal imaging device, wherein the processor circuit is configured to: obtain an enhanced stent deployment extraluminal image, wherein the enhanced stent deployment extraluminal image depicts a stent positioned within a body lumen of a patient, wherein a visual appearance of the stent in the enhanced stent deployment extraluminal image is enhanced relative to other portions of the enhanced stent deployment extraluminal image; receive a plurality of intraluminal images obtained by the intraluminal imaging device during the movement of the intraluminal imaging device within the body lumen, wherein a first set of the plurality of intraluminal images obtained during the movement through the stent depicts the stent; co-register the plurality of intraluminal images to corresponding locations within the enhanced stent deployment extraluminal image; and output, to a display in communication with the processor circuit, a screen display comprising: the enhanced stent deployment extraluminal image; an intraluminal image of the first set of the plurality of intraluminal images.

In one aspect, the processor circuit is configured to provide the enhanced stent deployment extraluminal image in the screen display, in response to automatically identifying a stent within the intraluminal image. In one aspect, the enhanced stent deployment extraluminal image includes a marker identifying the location within the enhanced stent deployment extraluminal image corresponding to the intraluminal image. In one aspect, the processor circuit is further configured to determine an expansion score for one or more of the plurality of intraluminal images. In one aspect, the processor circuit is configured to automatically identify a stent edge within one or more of the plurality of intraluminal images. In one aspect, the processor circuit is configured to compare the expansion score of the one or more intraluminal images with a threshold expansion score. In one aspect, the processor circuit is configured to identify a second set of the plurality of intraluminal images corresponding to the expansion score exceeding the threshold expansion score. In one aspect, the enhanced stent deployment extraluminal image includes an indicator identifying one or more locations within the stent deployment extraluminal image corresponding to the expansion score exceeding the threshold expansion score. In one aspect, the processor circuit is further configured to receive a plurality of extraluminal images and the screen display further comprises an extraluminal image of the plurality of extraluminal images. In one aspect, the screen display further comprises a longitudinal view of the body lumen including the stent. In one aspect, the longitudinal view includes an indicator of a region of the stent corresponding to an expansion score which does not exceed a threshold expansion score. In one aspect, a length of body lumen depicted in the enhanced stent deployment extraluminal image comprises only a portion of the body lumen including the stent.

In an exemplary aspect, a method is provided. The method includes obtaining an enhanced stent deployment extraluminal image, wherein the enhanced stent deployment extraluminal image depicts a stent positioned within a body lumen of a patient, wherein a visual appearance of the stent in the enhanced stent deployment extraluminal image is enhanced relative to other portions of the enhanced stent deployment extraluminal image; receiving a plurality of intraluminal images obtained by an intraluminal imaging device during the movement of the intraluminal imaging device within the body lumen, wherein a first set of the plurality of intraluminal images obtained during the movement through the stent depicts the stent; co-registering the plurality of intraluminal images to corresponding locations within the enhanced stent deployment extraluminal image; and outputting, to a display in communication with the processor circuit, a screen display comprising: the enhanced stent deployment extraluminal image; and an intraluminal image of the first set of the plurality of intraluminal images.

In an exemplary aspect, a system is provided. The system includes an intravascular ultrasound (IVUS) imaging device; a processor circuit configured for communication with an x-ray imaging device and the IVUS imaging device, wherein the processor circuit is configured to: obtain an enhanced stent deployment x-ray image, wherein the enhanced stent deployment x-ray image depicts a stent positioned within a body lumen of a patient, wherein a visual appearance of the stent in the enhanced stent deployment x-ray image is enhanced relative to other portions of the enhanced stent deployment x-ray image; receive a plurality of x-ray images obtained by the x-ray imaging device; receive a plurality of IVUS images obtained by the IVUS imaging device during the movement of the IVUS imaging device within the body lumen, wherein a first set of the plurality of IVUS images obtained during the movement through the stent depicts the stent; co-register the plurality of IVUS images to corresponding locations within the enhanced stent deployment x-ray image; generate a longitudinal view of the body lumen based on the plurality of IVUS images; and output, to a display in communication with the processor circuit, a screen display comprising: the enhanced stent deployment x-ray image; an intraluminal image of the first set of the plurality of IVUS images; the longitudinal view; and an x-ray image of the plurality of x-ray images.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 12 is a flow diagram of a method of coregistering IVUS imaging data to a stent-enhanced image, according to aspects of the present disclosure.

DETAILED DESCRIPTION

Figure 1:
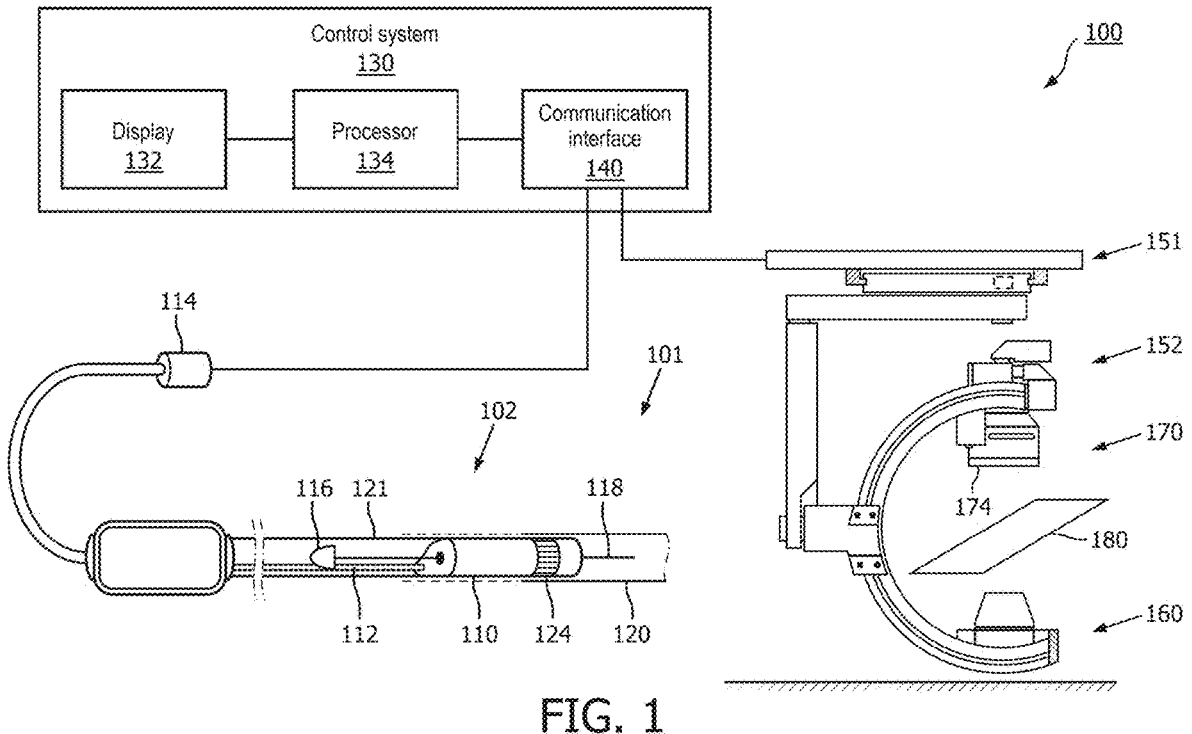
FIG. 1 is a schematic diagram of an intraluminal imaging and x-ray system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a schematic diagram of an intraluminal imaging and x-ray system 100, according to aspects of the present disclosure. In some embodiments, the intraluminal imaging and x-ray system 100 may include two separate systems or be a combination of two systems: an intraluminal sensing system 101 and an extraluminal imaging system 151. The intraluminal sensing system 101 obtains medical data about a patient's body while the intraluminal device 102 is positioned inside the patient's body. For example, the intraluminal sensing system 101 can control the intraluminal device 102 to obtain intraluminal images of the inside of the patient's body while the intraluminal device 102 is inside the patient's body. The extraluminal imaging system 151 obtains medical data about the patient's body while the extraluminal imaging device 152 is positioned outside the patient's body. For example, the extraluminal imaging system 151 can control extraluminal imaging device 152 to obtain extraluminal images of the inside of the patient's body while the extraluminal imaging device 152 is outside the patient's body.

The intraluminal imaging system 101 may be in communication with the extraluminal imaging system 151 through any suitable components. Such communication may be established through a wired cable, through a wireless signal, or by any other means. In addition, the intraluminal imaging system 101 may be in continuous communication with the x-ray system 151 or may be in intermittent communication. For example, the two systems may be brought into temporary communication via a wired cable, or brought into communication via a wireless communication, or through any other suitable means at some point before, after, or during an examination. In addition, the intraluminal system 101 may receive data such as x-ray images, annotated x-ray images, metrics calculated with the x-ray imaging system 151, information regarding dates and times of examinations, types and/or severity of patient conditions or diagnoses, patient history or other patient information, or any suitable data or information from the x-ray imaging system 151. The x-ray imaging system 151 may also receive any of these data from the intraluminal imaging system 101. In some embodiments, and as shown in FIG. 1, the intraluminal imaging system 101 and the x-ray imaging system 151 may be in communication with the same control system 130. In this embodiment, both systems may be in communication with the same display 132, processor 134, and communication interface 140 shown as well as in communication with any other components implemented within the control system 130.

In some embodiments, the system 100 may not include a control system 130 in communication with the intraluminal imaging system 101 and the x-ray imaging system 151. Instead, the system 100 may include two separate control systems. For example, one control system may be in communication with or be a part of the intraluminal imaging system 101 and an additional separate control system may be in communication with or be a part of the x-ray imaging system 151. In this embodiment, the separate systems of both the intraluminal imaging system 101 and the x-ray imaging system 151 may be similar to the control system 130. For example, each control system may include various components or systems such as a communication interface, processor, and/or a display. In this embodiment, the control system of the intraluminal imaging system 101 may perform any or all of the coregistration steps described in the present disclosure. Alternatively, the control system of the x-ray imaging system 151 may perform the coregistration steps described.

The intraluminal imaging system 101 can be an ultrasound imaging system. In some instances, the intraluminal imaging system 101 can be an intravascular ultrasound (IVUS) imaging system. The intraluminal imaging system 101 may include an intraluminal imaging device 102, such as a catheter, guide wire, or guide catheter, in communication with the control system 130. The control system 130 may include a display 132, a processor 134, and a communication interface 140 among other components. The intraluminal imaging device 102 can be an ultrasound imaging device. In some instances, the device 102 can be an IVUS imaging device, such as a solid-state IVUS device.

At a high level, the IVUS device 102 emits ultrasonic energy from a transducer array 124 included in a scanner assembly, also referred to as an IVUS imaging assembly, mounted near a distal end of the catheter device. The ultrasonic energy is reflected by tissue structures in the surrounding medium, such as a vessel 120, or another body lumen surrounding the scanner assembly 110, and the ultrasound echo signals are received by the transducer array 124. In that regard, the device 102 can be sized, shaped, or otherwise configured to be positioned within the body lumen of a patient. The communication interface 140 transfers the received echo signals to the processor 134 of the control system 130 where the ultrasound image (including flow information in some embodiments) is reconstructed and displayed on the display 132. The control system 130, including the processor 134, can be operable to facilitate the features of the IVUS imaging system 101 described herein. For example, the processor 134 can execute computer readable instructions stored on the non-transitory tangible computer readable medium.

The communication interface 140 facilitates communication of signals between the control system 130 and the scanner assembly 110 included in the IVUS device 102. This communication includes the steps of: (1) providing commands to integrated circuit controller chip(s) included in the scanner assembly 110 to select the particular transducer array element(s), or acoustic element(s), to be used for transmit and receive, (2) providing the transmit trigger signals to the integrated circuit controller chip(s) included in the scanner assembly 110 to activate the transmitter circuitry to generate an electrical pulse to excite the selected transducer array element(s), and/or (3) accepting amplified echo signals received from the selected transducer array element(s) via amplifiers included on the integrated circuit controller chip(s) of the scanner assembly 110. In some embodiments, the communication interface 140 performs preliminary processing of the echo data prior to relaying the data to the processor 134. In examples of such embodiments, the communication interface 140 performs amplification, filtering, and/or aggregating of the data. In an embodiment, the communication interface 140 also supplies high- and low-voltage DC power to support operation of the device 102 including circuitry within the scanner assembly 110.

The processor 134 receives the echo data from the scanner assembly 110 by way of the communication interface 140 and processes the data to reconstruct an image of the tissue structures in the medium surrounding the scanner assembly 110. The processor 134 outputs image data such that an image of the lumen 120, such as a cross-sectional image of the vessel 120, is displayed on the display 132. The lumen 120 may represent fluid filled or surrounded structures, both natural and man-made. The lumen 120 may be within a body of a patient. The lumen 120 may be a blood vessel, such as an artery or a vein of a patient's vascular system, including cardiac vasculature, peripheral vasculature, neural vasculature, renal vasculature, and/or any other suitable lumen inside the body. For example, the device 102 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood, chambers or other parts of the heart, and/or other systems of the body. In addition to natural structures, the device 102 may be used to examine man-made structures such as, but without limitation, heart valves, stents, shunts, filters and other devices.

In some embodiments, the IVUS device includes some features similar to traditional solid-state IVUS catheters, such as the EagleEye® catheter, Visions PV 0.014P RX catheter, Visions PV 0.018 catheter, Visions PV 0.035, and Pioneer Plus catheter, each of which are available from Koninklijke Philips N.V, and those disclosed in U.S. Pat. No. 7,846,101 hereby incorporated by reference in its entirety. For example, the IVUS device 102 includes the scanner assembly 110 near a distal end of the device 102 and a transmission line bundle 112 extending along the longitudinal body of the device 102. The transmission line bundle or cable 112 can include a plurality of conductors, including one, two, three, four, five, six, seven, or more conductors. It is understood that any suitable gauge wire can be used for the conductors. In an embodiment, the cable 112 can include a four-conductor transmission line arrangement with, e.g., 41 AWG gauge wires. In an embodiment, the cable 112 can include a seven-conductor transmission line arrangement utilizing, e.g., 44 AWG gauge wires. In some embodiments, 43 AWG gauge wires can be used.

The transmission line bundle 112 terminates in a patient interface module (PIM) connector 114 at a proximal end of the device 102. The PIM connector 114 electrically couples the transmission line bundle 112 to the communication interface 140 and physically couples the IVUS device 102 to the communication interface 140. In some embodiments, the communication interface 140 may be a PIM. In an embodiment, the IVUS device 102 further includes a guide wire exit port 116. Accordingly, in some instances the IVUS device 102 is a rapid-exchange catheter. The guide wire exit port 116 allows a guide wire 118 to be inserted towards the distal end to direct the device 102 through the vessel 120.

In some embodiments, the intraluminal imaging device 102 may acquire intravascular images of any suitable imaging modality, including optical coherence tomography (OCT) and intravascular photoacoustic (IVPA).

In some embodiments, the intraluminal device 102 is a pressure sensing device (e.g., pressure-sensing guidewire) that obtains intraluminal (e.g., intravascular) pressure data, and the intraluminal system 101 is an intravascular pressure sensing system that determines pressure ratios based on the pressure data, such as fractional flow reserve (FFR), instantaneous wave-free ratio (iFR), and/or other suitable ratio between distal pressure and proximal/aortic pressure (Pd/Pa). In some embodiments, the intraluminal device 102 is a flow sensing device (e.g., flow-sensing guidewire) that obtains intraluminal (e.g., intravascular) flow data, and the intraluminal system 101 is an intravascular flow sensing system that determines flow-related values based on the pressure data, such as coronary flow reserve (CFR), flow velocity, flow volume, etc.

The x-ray imaging system 151 may include an x-ray imaging apparatus or device 152 configured to perform x-ray imaging, angiography, fluoroscopy, radiography, venography, among other imaging techniques. The x-ray imaging system 151 can generate a single x-ray image (e.g., an angiogram or venogram) or multiple (e.g., two or more) x-ray images (e.g., a video and/or fluoroscopic image stream) based on x-ray image data collected by the x-ray device 152. The x-ray imaging device 152 may be of any suitable type, for example, it may be a stationary x-ray system such as a fixed c-arm x-ray device, a mobile c-arm x-ray device, a straight arm x-ray device, or a u-arm device. The x-ray imaging device 152 may additionally be any suitable mobile device. The x-ray imaging device 152 may also be in communication with the control system 130. In some embodiments, the x-ray system 151 may include a digital radiography device or any other suitable device.

The x-ray device 152 as shown in FIG. 1 includes an x-ray source 160 and an x-ray detector 170 including an input screen 174. The x-ray source 160 and the detector 170 may be mounted at a mutual distance. Positioned between the x-ray source 160 and the x-ray detector 170 may be an anatomy of a patient or object 180. For example, the anatomy of the patient (including the vessel 120) can be positioned between the x-ray source 160 and the x-ray detector 170.

The x-ray source 160 may include an x-ray tube adapted to generate x-rays. Some aspects of the x-ray source 160 may include one or more vacuum tubes including a cathode in connection with a negative lead of a high-voltage power source and an anode in connection with a positive lead of the same power source. The cathode of the x-ray source 160 may additionally include a filament. The filament may be of any suitable type or constructed of any suitable material, including tungsten or rhenium tungsten, and may be positioned within a recessed region of the cathode. One function of the cathode may be to expel electrons from the high voltage power source and focus them into a well-defined beam aimed at the anode. The anode may also be constructed of any suitable material and may be configured to create x-radiation from the emitted electrons of the cathode. In addition, the anode may dissipate heat created in the process of generating x-radiation. The anode may be shaped as a beveled disk and, in some embodiments, may be rotated via an electric motor. The cathode and anode of the x-ray source 160 may be housed in an airtight enclosure, sometimes referred to as an envelope.

In some embodiments, the x-ray source 160 may include a radiation object focus which influences the visibility of an image. The radiation object focus may be selected by a user of the system 100 or by a manufacture of the system 100 based on characteristics such as blurring, visibility, heat-dissipating capacity, or other characteristics. In some embodiments, an operator or user of the system 100 may switch between different provided radiation object foci in a point-of-care setting.

The detector 170 may be configured to acquire x-ray images and may include the input screen 174. The input screen 174 may include one or more intensifying screens configured to absorb x-ray energy and convert the energy to light. The light may in turn expose a film. The input screen 174 may be used to convert x-ray energy to light in embodiments in which the film may be more sensitive to light than x-radiation. Different types of intensifying screens within the image intensifier may be selected depending on the region of a patient to be imaged, requirements for image detail and/or patient exposure, or any other factors. Intensifying screens may be constructed of any suitable materials, including barium lead sulfate, barium strontium sulfate, barium fluorochloride, yttrium oxysulfide, or any other suitable material. The input screen 374 may be a fluorescent screen or a film positioned directly adjacent to a fluorescent screen. In some embodiments, the input screen 374 may also include a protective screen to shield circuitry or components within the detector 370 from the surrounding environment. In some embodiments, the x-ray detector 170 may include a flat panel detector (FPD). The detector 170 may be an indirect conversion FPD or a direct conversion FPD. The detector 170 may also include charge-coupled devices (CCDs). The x-ray detector 370 may additionally be referred to as an x-ray sensor.

The object 180 may be any suitable object to be imaged. In an exemplary embodiment, the object may be the anatomy of a patient. More specifically, the anatomy to be imaged may include chest, abdomen, the pelvic region, neck, legs, head, feet, a region with cardiac vasculature, or a region containing the peripheral vasculature of a patient and may include various anatomical structures such as, but not limited to, organs, tissue, blood vessels and blood, gases, or any other anatomical structures or objects. In other embodiments, the object may be or include man-made structures.

In some embodiments, the x-ray imaging system 151 may be configured to obtain x-ray images without contrast. In some embodiments, the x-ray imaging system 151 may be configured to obtain x-ray images with contrast (e.g., angiogram or venogram). In such embodiments, a contrast agent or x-ray dye may be introduced to a patient's anatomy before imaging. The contrast agent may also be referred to as a radiocontrast agent, contrast material, contrast dye, or contrast media. The contrast dye may be of any suitable material, chemical, or compound and may be a liquid, powder, paste, tablet, or of any other suitable form. For example, the contrast dye may be iodine-based compounds, barium sulfate compounds, gadolinium-based compounds, or any other suitable compounds. The contrast agent may be used to enhance the visibility of internal fluids or structures within a patient's anatomy. The contrast agent may absorb external x-rays, resulting in decreased exposure on the x-ray detector 170.

In some embodiments, the extraluminal imaging system 151 could be any suitable extraluminal imaging device, such as computed tomography (CT) or magnetic resonance imaging (MRI).

When the control system 130 is in communication with the x-ray system 151, the communication interface 140 facilitates communication of signals between the control system 130 and the x-ray device 152. This communication includes providing control commands to the x-ray source 160 and/or the x-ray detector 170 of the x-ray device 152 and receiving data from the x-ray device 152. In some embodiments, the communication interface 140 performs preliminary processing of the x-ray data prior to relaying the data to the processor 134. In examples of such embodiments, the communication interface 140 may perform amplification, filtering, and/or aggregating of the data. In an embodiment, the communication interface 140 also supplies highand low-voltage DC power to support operation of the device 152 including circuitry within the device.

The processor 134 receives the x-ray data from the x-ray device 152 by way of the communication interface 140 and processes the data to reconstruct an image of the anatomy being imaged. The processor 134 outputs image data such that an image is displayed on the display 132. In an embodiment in which the contrast agent is introduced to the anatomy of a patient and a venogram is to be generated, the particular areas of interest to be imaged may be one or more blood vessels or other section or part of the human vasculature. The contrast agent may identify fluid filled structures, both natural and/or man-made, such as arteries or veins of a patient's vascular system, including cardiac vasculature, peripheral vasculature, neural vasculature, renal vasculature, and/or any other suitable lumen inside the body. For example, the x-ray device 152 may be used to examine any number of anatomical locations and tissue types, including without limitation all the organs, fluids, or other structures or parts of an anatomy previously mentioned. In addition to natural structures, the x-ray device 152 may be used to examine man-made structures such as any of the previously mentioned structures.

The processor 134 may be configured to receive an x-ray image that was stored by the x-ray imaging device 152 during a clinical procedure. The images may be further enhanced by other information such as patient history, patient record, IVUS imaging, pre-operative ultrasound imaging, pre-operative CT, or any other suitable data.

Figure 2:
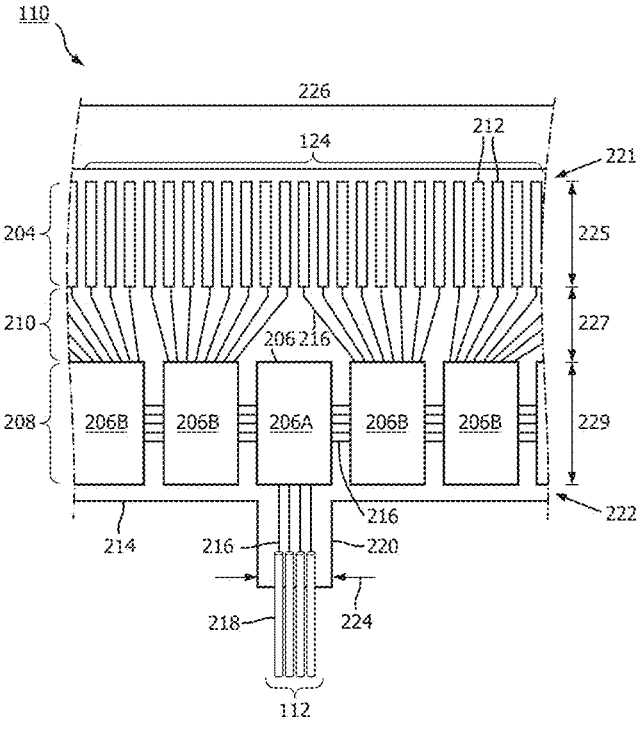
FIG. 2 is a diagrammatic top view of an ultrasound imaging assembly in a flat configuration, according to aspects of the present disclosure.

FIG. 2 is a diagrammatic top view of a portion of a flexible assembly 110, according to aspects of the present disclosure. The flexible assembly 110 includes a transducer array 124 formed in a transducer region 204 and transducer control logic dies 206 (including dies 206A and 206B) formed in a control region 208, with a transition region 210 disposed therebetween. The transducer array 124 includes an array of ultrasound transducer elements 212. The transducer control logic dies 206 are mounted on a flexible substrate 214 into which the transducer elements 212 have been previously integrated. The flexible substrate 214 is shown in a flat configuration in FIG. 2. Though six control logic dies 206 are shown in FIG. 2, any number of control logic dies 206 may be used. For example, one, two, three, four, five, six, seven, eight, nine, ten, or more control logic dies 206 may be used.

The flexible substrate 214, on which the transducer control logic dies 206 and the transducer elements 212 are mounted, provides structural support and interconnects for electrical coupling. The flexible substrate 214 may be constructed to include a film layer of a flexible polyimide material such as KAPTON™ (trademark of DuPont). Other suitable materials include polyester films, polyimide films, polyethylene napthalate films, or polyetherimide films, liquid crystal polymer, other flexible printed semiconductor substrates as well as products such as Upilex® (registered trademark of Ube Industries) and TEFLON® (registered trademark of E.I. du Pont). In the flat configuration illustrated in FIG. 2, the flexible substrate 214 has a generally rectangular shape. As shown and described herein, the flexible substrate 214 is configured to be wrapped around a support member 230 (FIG. 3) in some instances. Therefore, the thickness of the film layer of the flexible substrate 214 is generally related to the degree of curvature in the final assembled flexible assembly 110. In some embodiments, the film layer is between 5 μm and 100 μm, with some particular embodiments being between 5 μm and 25.1 μm, e.g., 6 μm.

The set of transducer control logic dies 206 is a non-limiting example of a control circuit. The transducer region 204 is disposed at a distal portion 221 of the flexible substrate 214. The control region 208 is disposed at a proximal portion 222 of the flexible substrate 214. The transition region 210 is disposed between the control region 208 and the transducer region 204. Dimensions of the transducer region 204, the control region 208, and the transition region 210 (e.g., lengths 225, 227, 229) can vary in different embodiments. In some embodiments, the lengths 225, 227, 229 can be substantially similar or, the length 227 of the transition region 210 may be less than lengths 225 and 229, the length 227 of the transition region 210 can be greater than lengths 225, 229 of the transducer region and controller region, respectively.

The control logic dies 206 are not necessarily homogenous. In some embodiments, a single controller is designated a master control logic die 206A and contains the communication interface for cable 112, between a processing system, e.g., processing system 106, and the flexible assembly 110. Accordingly, the master control circuit may include control logic that decodes control signals received over the cable 112, transmits control responses over the cable 112, amplifies echo signals, and/or transmits the echo signals over the cable 112. The remaining controllers are slave controllers 206B. The slave controllers 206B may include control logic that drives a plurality of transducer elements 512 positioned on a transducer element 212 to emit an ultrasonic signal and selects a transducer element 212 to receive an echo. In the depicted embodiment, the master controller 206A does not directly control any transducer elements 212. In other embodiments, the master controller 206A drives the same number of transducer elements 212 as the slave controllers 206B or drives a reduced set of transducer elements 212 as compared to the slave controllers 206B. In an exemplary embodiment, a single master controller 206A and eight slave controllers 206B are provided with eight transducers assigned to each slave controller 206B.

To electrically interconnect the control logic dies 206 and the transducer elements 212, in an embodiment, the flexible substrate 214 includes conductive traces 216 formed in the film layer that carry signals between the control logic dies 206 and the transducer elements 212. In particular, the conductive traces 216 providing communication between the control logic dies 206 and the transducer elements 212 extend along the flexible substrate 214 within the transition region 210. In some instances, the conductive traces 216 can also facilitate electrical communication between the master controller 206A and the slave controllers 206B. The conductive traces 216 can also provide a set of conductive pads that contact the conductors 218 of cable 112 when the conductors 218 of the cable 112 are mechanically and electrically coupled to the flexible substrate 214. Suitable materials for the conductive traces 216 include copper, gold, aluminum, silver, tantalum, nickel, and tin, and may be deposited on the flexible substrate 214 by processes such as sputtering, plating, and etching. In an embodiment, the flexible substrate 214 includes a chromium adhesion layer. The width and thickness of the conductive traces 216 are selected to provide proper conductivity and resilience when the flexible substrate 214 is rolled. In that regard, an exemplary range for the thickness of a conductive trace 216 and/or conductive pad is between 1-5 μm. For example, in an embodiment, 5 μm conductive traces 216 are separated by 5 μm of space. The width of a conductive trace 216 on the flexible substrate may be further determined by the width of the conductor 218 to be coupled to the trace or pad.

The flexible substrate 214 can include a conductor interface 220 in some embodiments. The conductor interface 220 can be in a location of the flexible substrate 214 where the conductors 218 of the cable 112 are coupled to the flexible substrate 214. For example, the bare conductors of the cable 112 are electrically coupled to the flexible substrate 214 at the conductor interface 220. The conductor interface 220 can be tab extending from the main body of flexible substrate 214. In that regard, the main body of the flexible substrate 214 can refer collectively to the transducer region 204, controller region 208, and the transition region 210. In the illustrated embodiment, the conductor interface 220 extends from the proximal portion 222 of the flexible substrate 214. In other embodiments, the conductor interface 220 is positioned at other parts of the flexible substrate 214, such as the distal portion 221, or the flexible substrate 214 may lack the conductor interface 220. A value of a dimension of the tab or conductor interface 220, such as a width 224, can be less than the value of a dimension of the main body of the flexible substrate 214, such as a width 226. In some embodiments, the substrate forming the conductor interface 220 is made of the same material(s) and/or is similarly flexible as the flexible substrate 214. In other embodiments, the conductor interface 220 is made of different materials and/or is comparatively more rigid than the flexible substrate 214. For example, the conductor interface 220 can be made of a plastic, thermoplastic, polymer, hard polymer, etc., including polyoxymethylene (e.g., DELRIN®), polyether ether ketone (PEEK), nylon, Liquid Crystal Polymer (LCP), and/or other suitable materials.

Figure 3:
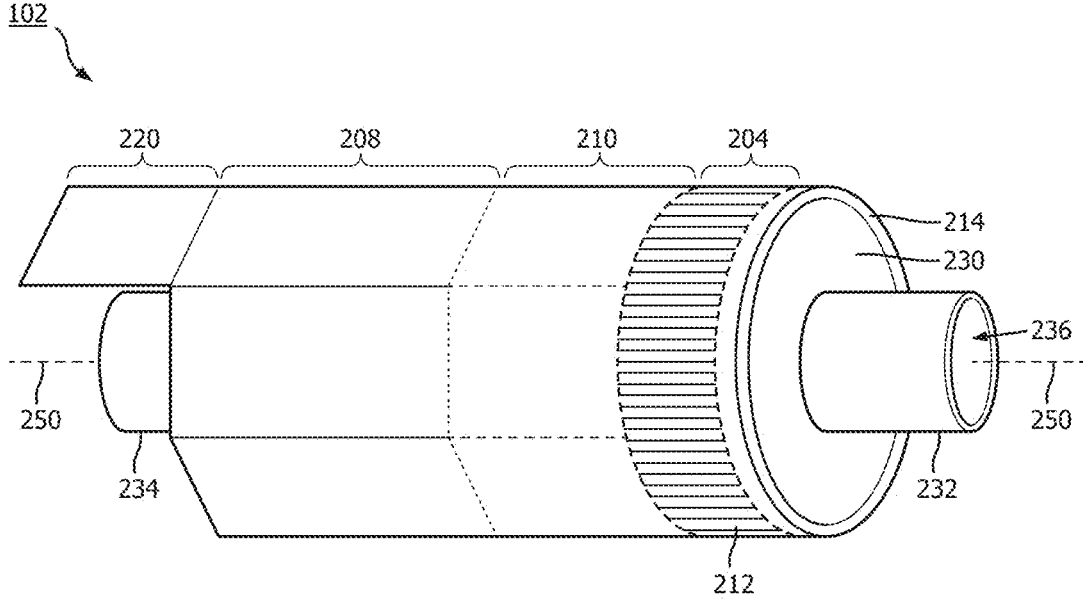
FIG. 3 is a diagrammatic perspective view of the ultrasound imaging assembly shown in FIG. 2 in a rolled configuration around a support member, according to aspects of the present disclosure.

FIG. 3 illustrates a perspective view of the scanner assembly 110 in a rolled configuration. In some instances, the flexible substrate 214 is transitioned from a flat configuration (FIG. 2) to a rolled or more cylindrical configuration (FIG. 3). For example, in some embodiments, techniques are utilized as disclosed in one or more of U.S. Pat. No. 6,776,763, titled "ULTRASONIC TRANSDUCER ARRAY AND METHOD OF MANUFACTURING THE SAME" and U.S. Pat. No. 7,226,417, titled "HIGH RESOLUTION INTRAVASCULAR ULTRASOUND SENSING ASSEMBLY HAVING A FLEXIBLE SUBSTRATE," each of which is hereby incorporated by reference in its entirety.

Depending on the application and embodiment of the presently disclosed invention, transducer elements 212 may be piezoelectric transducers, single crystal transducer, or PZT (lead zirconate titanate) transducers. In other embodiments, the transducer elements of transducer array 124 may be flexural transducers, piezoelectric micromachined ultrasonic transducers (PMUTs), capacitive micromachined ultrasonic transducers (CMUTs), or any other suitable type of transducer element. In such embodiments, transducer elements 212 may comprise an elongate semiconductor material or other suitable material that allows micromachining or similar methods of disposing extremely small elements or circuitry on a substrate.

In some embodiments, the transducer elements 212 and the controllers 206 can be positioned in an annular configuration, such as a circular configuration or in a polygon configuration, around a longitudinal axis 250 of a support member 230. It is understood that the longitudinal axis 250 of the support member 230 may also be referred to as the longitudinal axis of the scanner assembly 110, the flexible elongate member 121, or the device 102. For example, a cross-sectional profile of the imaging assembly 110 at the transducer elements 212 and/or the controllers 206 can be a circle or a polygon. Any suitable annular polygon shape can be implemented, such as one based on the number of controllers or transducers, flexibility of the controllers or transducers, etc. Some examples may include a pentagon, hexagon, heptagon, octagon, nonagon, decagon, etc. In some examples, the transducer controllers 206 may be used for controlling the ultrasound transducers 512 of transducer elements 212 to obtain imaging data associated with the vessel 120.

The support member 230 can be referenced as a unibody in some instances. The support member 230 can be composed of a metallic material, such as stainless steel, or a non-metallic material, such as a plastic or polymer as described in U.S. Provisional Application No. 61/985,220, "Pre-Doped Solid Substrate for Intravascular Devices," filed Apr. 28, 2014, the entirety of which is hereby incorporated by reference herein. In some embodiments, support member 230 may be composed of 303 stainless steel. The support member 230 can be a ferrule having a distal flange or portion 232 and a proximal flange or portion 234. The support member 230 can be tubular in shape and define a lumen 236 extending longitudinally therethrough. The lumen 236 can be sized and shaped to receive the guide wire 118. The support member 230 can be manufactured using any suitable process. For example, the support member 230 can be machined and/or electrochemically machined or laser milled, such as by removing material from a blank to shape the support member 230, or molded, such as by an injection molding process or a micro injection molding process.

Figure 4:
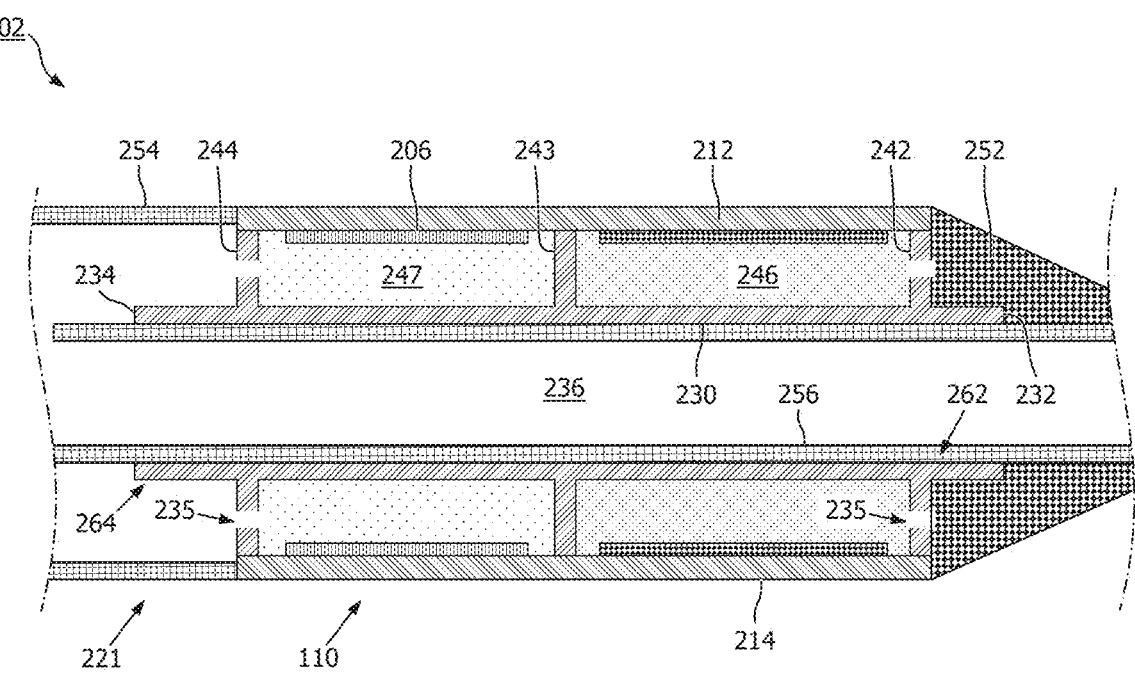
FIG. 4 is a diagrammatic cross-sectional side view of the ultrasound imaging assembly shown in FIG. 3, according to aspects of the present disclosure.

Referring now to FIG. 4, shown therein is a diagrammatic cross-sectional side view of a distal portion of the intraluminal imaging device 102, including the flexible substrate 214 and the support member 230, according to aspects of the present disclosure. The lumen 236 may be connected with the entry/exit port 116 and is sized and shaped to receive the guide wire 118 (FIG. 1). In some embodiments, the support member 230 may be integrally formed as a unitary structure, while in other embodiments the support member 230 may be formed of different components, such as a ferrule and stands 242, 243, and 244, that are fixedly coupled to one another. In some cases, the support member 230 and/or one or more components thereof may be completely integrated with inner member 256. In some cases, the inner member 256 and the support member 230 may be joined as one, e.g., in the case of a polymer support member.

Stands 242, 243, and 244 that extend vertically are provided at the distal, central, and proximal portions respectively, of the support member 230. The stands 242, 243, and 244 elevate and support the distal, central, and proximal portions of the flexible substrate 214. In that regard, portions of the flexible substrate 214, such as the transducer portion 204 (or transducer region 204), can be spaced from a central body portion of the support member 230 extending between the stands 242, 243, and 244. The stands 242, 243, 244 can have the same outer diameter or different outer diameters. For example, the distal stand 242 can have a larger or smaller outer diameter than the central stand 243 and/or proximal stand 244 and can also have special features for rotational alignment as well as control chip placement and connection.

To improve acoustic performance, the cavity between the transducer array 212 and the surface of the support member 230 may be filled with an acoustic backing material 246. The liquid backing material 246 can be introduced between the flexible substrate 214 and the support member 230 via passageway 235 in the stand 242, or through additional recesses as will be discussed in more detail hereafter. The backing material 246 may serve to attenuate ultrasound energy emitted by the transducer array 212 that propagates in the undesired, inward direction.

The cavity between the circuit controller chips 206 and the surface of the support member 230 may be filled with an underfill material 247. The underfill material 247 may be an adhesive material (e.g. an epoxy) which provides structural support for the circuit controller chips 206 and/or the flexible substrate 214. The underfill 247 may additionally be any suitable material.

In some embodiments, the central body portion of the support member can include recesses allowing fluid communication between the lumen of the unibody and the cavities between the flexible substrate 214 and the support member 230. Acoustic backing material 246 and/or underfill material 247 can be introduced via the cavities (during an assembly process, prior to the inner member 256 extending through the lumen of the unibody. In some embodiments, suction can be applied via the passageways 235 of one of the stands 242, 244, or to any other suitable recess while the liquid backing material 246 is fed between the flexible substrate 214 and the support member 230 via the passageways 235 of the other of the stands 242, 244, or any other suitable recess. The backing material can be cured to allow it to solidify and set. In various embodiments, the support member 230 includes more than three stands 242, 243, and 244, only one or two of the stands 242, 243, 244, or none of the stands. In that regard the support member 230 can have an increased diameter distal portion 262 and/or increased diameter proximal portion 264 that is sized and shaped to elevate and support the distal and/or proximal portions of the flexible substrate 214.

The support member 230 can be substantially cylindrical in some embodiments. Other shapes of the support member 230 are also contemplated including geometrical, non-geometrical, symmetrical, non-symmetrical, cross-sectional profiles. As the term is used herein, the shape of the support member 230 may reference a cross-sectional profile of the support member 230. Different portions of the support member 230 can be variously shaped in other embodiments. For example, the proximal portion 264 can have a larger outer diameter than the outer diameters of the distal portion 262 or a central portion extending between the distal and proximal portions 262, 264. In some embodiments, an inner diameter of the support member 230 (e.g., the diameter of the lumen 236) can correspondingly increase or decrease as the outer diameter changes. In other embodiments, the inner diameter of the support member 230 remains the same despite variations in the outer diameter.

A proximal inner member 256 and a proximal outer member 254 are coupled to the proximal portion 264 of the support member 230. The proximal inner member 256 and/or the proximal outer member 254 can comprise a flexible elongate member. The proximal inner member 256 can be received within a proximal flange 234. The proximal outer member 254 abuts and is in contact with the proximal end of flexible substrate 214. A distal tip member 252 is coupled to the distal portion 262 of the support member 230. For example, the distal member 252 is positioned around the distal flange 232. The tip member 252 can abut and be in contact with the distal end of flexible substrate 214 and the stand 242. In other embodiments, the proximal end of the tip member 252 may be received within the distal end of the flexible substrate 214 in its rolled configuration. In some embodiments there may be a gap between the flexible substrate 214 and the tip member 252. The distal member 252 can be the distal-most component of the intraluminal imaging device 102. The distal tip member 252 may be a flexible, polymeric component that defines the distal-most end of the imaging device 102. The distal tip member 252 may additionally define a lumen in communication with the lumen 236 defined by support member 230. The guide wire 118 may extend through lumen 236 as well as the lumen defined by the tip member 252.

One or more adhesives can be disposed between various components at the distal portion of the intraluminal imaging device 102. For example, one or more of the flexible substrate 214, the support member 230, the distal member 252, the proximal inner member 256, the transducer array 212, and/or the proximal outer member 254 can be coupled to one another via an adhesive. Stated differently, the adhesive can be in contact with e.g. the transducer array 212, the flexible substrate 214, the support member 230, the distal member 252, the proximal inner member 256, and/or the proximal outer member 254, among other components.

Figure 5:
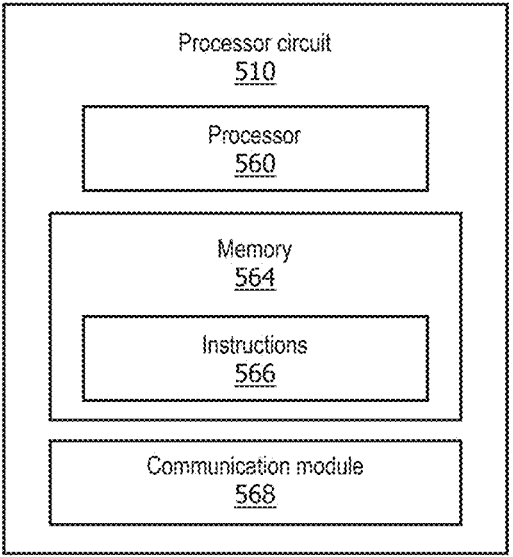
FIG. 5 is a schematic diagram of a processor circuit, according to aspects of the present disclosure.

FIG. 5 is a schematic diagram of a processor circuit, according to aspects of the present disclosure. The processor circuit 510 may be implemented in the control system 130 of FIG. 1, the intraluminal imaging system 101, and/or the x-ray imaging system 151, or any other suitable location. In an example, the processor circuit 510 may be in communication with intraluminal imaging device 102, the x-ray imaging device 152, the display 132 within the system 100. The processor circuit 510 may include the processor 134 and/or the communication interface 140 (FIG. 1). One or more processor circuits 510 are configured to execute the operations described herein. As shown, the processor circuit 510 may include a processor 560, a memory 564, and a communication module 568. These elements may be in direct or indirect communication with each other, for example via one or more buses.

The processor 560 may include a CPU, a GPU, a DSP, an application-specific integrated circuit (ASIC), a controller, an FPGA, another hardware device, a firmware device, or any combination thereof configured to perform the operations described herein. The processor 560 may also be implemented as a combination of computing devices, e.g., a combination of a DSP and a microprocessor, a plurality of microprocessors, one or more microprocessors in conjunction with a DSP core, or any other such configuration.

The memory 564 may include a cache memory (e.g., a cache memory of the processor 560), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In an embodiment, the memory 564 includes a non-transitory computer-readable medium. The memory 564 may store instructions 566. The instructions 566 may include instructions that, when executed by the processor 560, cause the processor 560 to perform the operations described herein with reference to the probe 110 and/or the host 130 (FIG. 1). Instructions 566 may also be referred to as code. The terms "instructions" and "code" should be interpreted broadly to include any type of computer-readable statement(s). For example, the terms "instructions" and "code" may refer to one or more programs, routines, subroutines, functions, procedures, etc. "Instructions" and "code" may include a single computer-readable statement or many computer-readable statements.

The communication module 568 can include any electronic circuitry and/or logic circuitry to facilitate direct or indirect communication of data between the processor circuit 510, the probe 110, and/or the display 132 and/or display 132. In that regard, the communication module 568 can be an input/output (I/O) device. In some instances, the communication module 568 facilitates direct or indirect communication between various elements of the processor circuit 510 and/or the probe 110 (FIG. 1) and/or the host 130 (FIG. 1).

Figure 6:
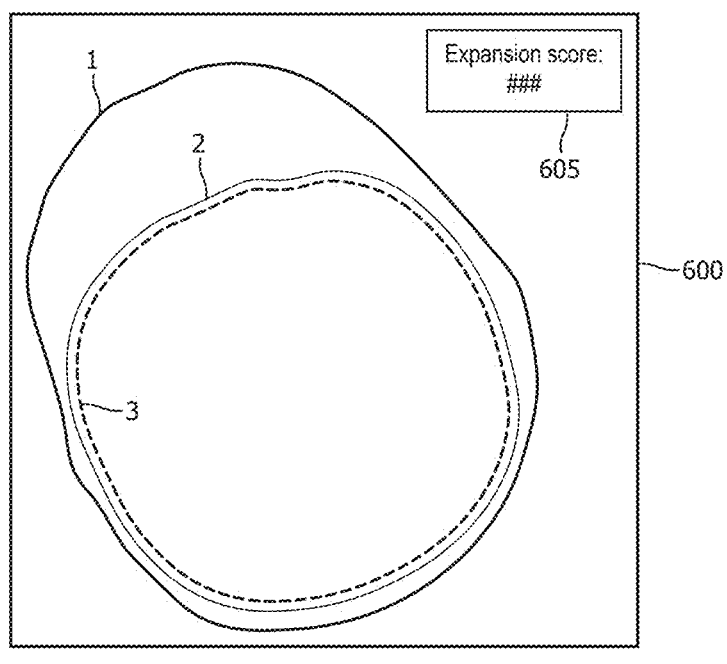
FIG. 6 is a diagrammatic view of an intravascular image, according to aspects of the present disclosure.

FIG. 6 is a diagrammatic view of an intravascular image 600, according to aspects of the present disclosure. The image 600 may be received by the intraluminal imaging system 101 by, for example, the device 102. In one example, the intraluminal image 600 may be an IVUS image. Steps may include performing a post stent automatic quantification of lumen/EEL (vessel wall) and/or minimum stent area and/or identification of stent edges.

In some embodiments, the processor circuit 510 may analyze each IVUS image acquired with the intraluminal imaging system 101. In some embodiments, the processor circuit 510 may receive an IVUS image (e.g., the image 600) of a region of the vessel which includes a treatment device, such as a stent. In some embodiments, the processor circuit 510 may be configured to identify a vessel wall 610, a lumen boundary 620, and a stent edge 640 within each image. The circuit 510 may identify these structures by any suitable means. For example, the circuit 510 may automatically identify a vessel wall 610, a lumen boundary 620, and/or a stent edge 640 of an IVUS image, such as the image 600. Examples of border detection, image processing, image analysis, and/or pattern recognition include U.S. Pat. No. 6,200,268 entitled "VASCULAR PLAQUE CHARACTERIZATION" issued Mar. 13, 2001 with D. Geoffrey Vince, Barry D. Kuban and Anuja Nair as inventors, U.S. Pat. No. 6,381,350 entitled "INTRAVASCULAR ULTRASONIC ANALYSIS USING ACTIVE CONTOUR METHOD AND SYSTEM" issued Apr. 30, 2002 with Jon D. Klingensmith, D. Geoffrey Vince and Raj Shekhar as inventors, U.S. Pat. No. 7,074,188 entitled "SYSTEM AND METHOD OF CHARACTERIZING VASCULAR TISSUE" issued Jul. 11, 2006 with Anuja Nair, D. Geoffrey Vince, Jon D. Klingensmith and Barry D. Kuban as inventors, U.S. Pat. No. 7,175,597 entitled "NON-INVASIVE TISSUE CHARACTERIZATION SYSTEM AND METHOD" issued Feb. 13, 2007 with D. Geoffrey Vince, Anuja Nair and Jon D. Klingensmith as inventors, U.S. Pat. No. 7,215,802 entitled "SYSTEM AND METHOD FOR VASCULAR BORDER DETECTION" issued May 8, 2007 with Jon D. Klingensmith, Anuja Nair, Barry D. Kuban and D. Geoffrey Vince as inventors, U.S. Pat. No. 7,359,554 entitled "SYSTEM AND METHOD FOR IDENTIFYING A VASCULAR BORDER" issued Apr. 15, 2008 with Jon D. Klingensmith, D. Geoffrey Vince, Anuja Nair and Barry D. Kuban as inventors and U.S. Pat. No. 7,463,759 entitled "SYSTEM AND METHOD FOR VASCULAR BORDER DETECTION" issued Dec. 9, 2008 with Jon D. Klingensmith, Anuja Nair, Barry D. Kuban and D. Geoffrey Vince, as inventors, the teachings of which are hereby incorporated by reference herein in their entirety. In one example, the processor circuit 510 may also identify a stent boundary 640. The stent boundary 640 may also be referred to as a stent edge. The stent boundary 640 may represent a radial cross-sectional view of a stent positioned within the vessel shown in the image 600.

In some embodiments, the processor circuit 510 may use various image processing techniques to identify any of the vessel wall 1, the lumen boundary 2, and/or the stent boundary 3 within each IVUS image frame. For example, the processor circuit 510 may use an edge-detection technique. In other embodiments, the circuit 510 may employ other image processing techniques such as pixel-by-pixel analysis to determine transitions between light pixels and dark pixels, filtering, or any other suitable techniques.

In some embodiments, the vessel wall 610 may be associated with an external elastic membrane (EEL). For example, the processor circuit 510 may be configured to identify the EEL of a vessel wall for each given IVUS image. In some embodiments, the vessel wall 610 may be associated with any other part of the vessel. For example, the vessel wall 610 identified by the processor circuit 510 may be associated with an endothelium layer, a subendothelial layer, an internal elastic lamina, a tunica media layer, a tunica externa layer, or any other structure.

After the circuit 510 has identified a vessel wall 610, a lumen boundary 620, and a stent boundary 640 for locations corresponding to the presence of a stent, the circuit 510 may determine any number of measurements or metrics associated with the image 600. For example, the processor circuit 510 may be configured to calculate a cross-sectional area of the vessel 610, a cross-sectional area of the lumen 620, and/or a cross-sectional area of the stent 640. In some instances, the processor circuit 510 may calculate a plaque burden value associated with the IVUS image 600. A plaque burden may include a numerical representation of the amount of plaque present in a particular IVUS image. In one example, a plaque burden may convey a difference between a cross-sectional area of a vessel and a cross-sectional area of a lumen and may be conveyed as a ratio or a percentage. In some embodiments, a plaque burden value may correspond to a comparison of the cross-sectional area of the region 630, shown in FIG. 6, with the total cross-sectional area of the vessel wall 610.

In one example, the processor circuit 510 may additionally be configured to calculate a stent expansion score 605. For example, the processor circuit 510 may determine or receive various parameters or characteristics of the stent 640. The processor circuit 510 may determine or receive information relating to the type of stent shown in the image 600, including an expected length and/or diameter in both an expanded or unexpanded state, including dimensions of the stent or expected dimensions of the stent before and after deployment, among other parameters. Based on this or other information, the processor circuit 510 may make a determination of the effectiveness of expansion of the stent 640. For example, the processor circuit 510 may compare the measured cross-sectional area of the stent 640 as shown in the image 600 with an expected cross-sectional area of the stent. In other embodiments, the processor circuit 510 may also compare the cross-sectional shape of the stent boundary 640 with an expected cross-sectional shape of the stent. Any of these comparisons may include a comparison with accepted ranges of values, thresholds of values, or other methods of comparison.

In one example, the expansion score 605 may be a ratio or percentage. For example, the processor circuit 510 may divide the measured cross-sectional area of the stent 640 by the expected cross-sectional area of the stent. This value may be shown as a percentage and displayed overlaid over the image 600 as shown in FIG. 6 (e.g., the expansion score 605). In other embodiments, the processor circuit 510 may use other methods. In some embodiments, the expansion score 605 may include a ratio or percentage corresponding to the cross-sectional area or diameter of the stent and the cross-sectional area or diameter of the vessel wall or lumen. In some embodiments, the processor circuit 510 may implement various machine learning techniques trained with sets of images annotated by experts in the field to assign a stent expansion score 605 to a particular image 600.

It is noted that, in some embodiments, the image 600, or any received IVUS image, may not include a depiction of a stent. For example, the IVUS imaging device 102 may be pulled through various sections of the imaged vessel in which no stent is positioned. In such instances, the processor circuit 510 may not display a stent expansion score 605. In some implementations, the processor circuit 510 may be configured to automatically determine a stent expansion score in response to the processor circuit 510 recognizing and identifying a stent, such as the stent 640, within an IVUS image. Any of the disclosed algorithms of the present disclosure may be automatically activated when the system detects a stent whilst performing an IVUS pullback procedure.

Figure 7:
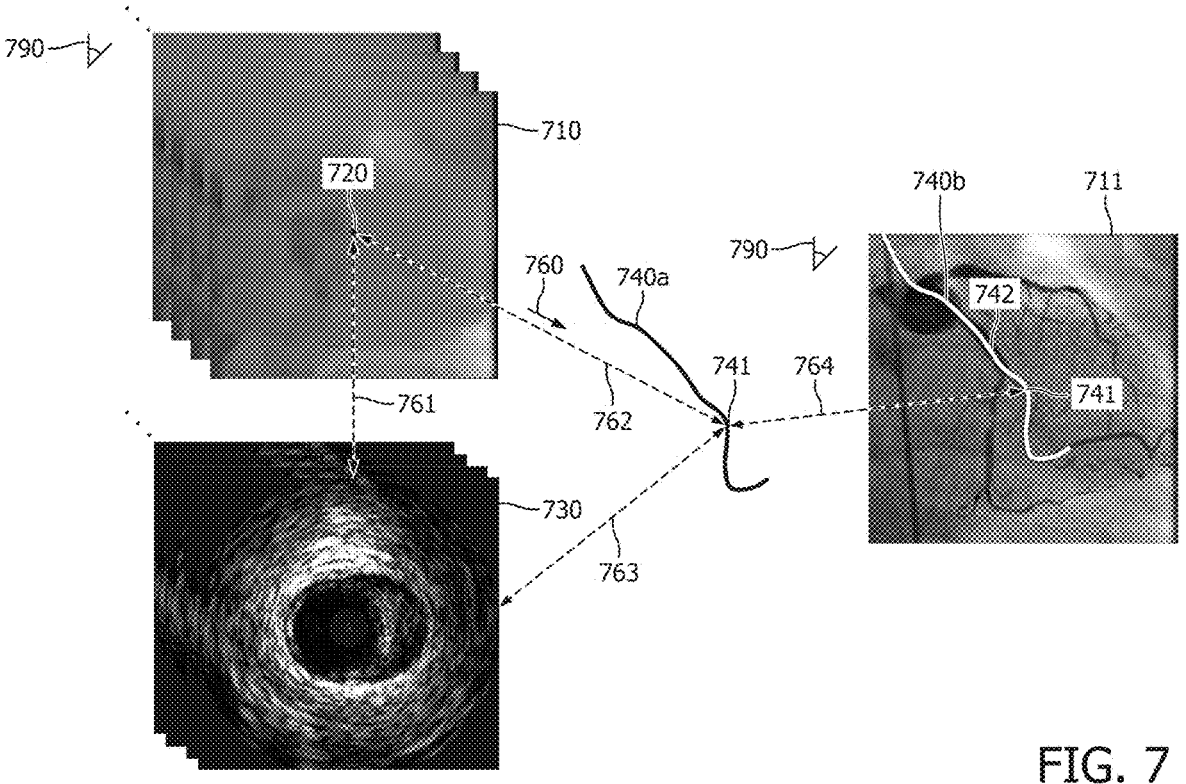
FIG. 7 is a diagrammatic view of a relationship between x-ray fluoroscopy images, intravascular ultrasound images, and a path defined by the motion of an intravascular imaging device, according to aspects of the present disclosure.

FIG. 7 is a diagrammatic view of a relationship between x-ray fluoroscopy images 710, intravascular ultrasound images 730, and a path 740a defined by the motion of an intravascular imaging device, according to aspects of the present disclosure. For the purposes of this disclosure, a no contrast x-ray image frame may refer to an x-ray image generated by an x-ray imaging system (e.g., the system 151 of FIG. 1) depicting a patient anatomy without a contrast agent within the vessels shown in the image. A contrast x-ray image frame may refer to an x-ray image generated by an x-ray imaging system (e.g., the system 151 of FIG. 1) depicting a patient anatomy with a contrast agent within the vessels shown in the image. In some embodiments, a no contrast image frame may also be referred to as a fluoroscopy image or a fluoroscopic image. A contrast image frame may also be referred to as an angiogram, an angiogram image, an angriographic image, a venogram, a venogram image, or a venographic image. As noted, any of the systems and methods described herein may be applicable to any type of lumen. For example, the systems and methods described may apply to the imaging and measurement of regions of a peripheral vasculature as well as regions of a coronary vasculature. Any descriptions of images within the present disclosure are not intended to limit the application of any aspect of the disclosure to a particular type of lumen either of a patient or any other structure.

FIG. 7 describes a method of coregistering intravascular data 730 including intravascular images with corresponding locations on one or more no contrast images 710 of the same region of a patient's anatomy. The methods described with reference to FIG. 7 may be employed by the processor circuit 510 to coregister IVUS images (e.g., the image 600 of FIG. 6) and associated data (e.g., the expansion score 605 of FIG. 6) with locations along a guidewire within the imaged vessel or locations along the vessel itself in embodiments in which a contrast agent is introduced to the imaged vessel. Steps may include performing an IVUS pullback procedure.

As part of a coregistration procedure, the patient anatomy may be imaged with an x-ray device while a physician performs a pullback with an intravascular device 720, e.g., while the intravascular device 720 moves through a blood vessel of the anatomy. The intravascular device may be substantially similar to the intravascular device 102 described with reference to FIG. 1. The x-ray device used to obtain the fluoroscopy images 710 may be substantially similar to the x-ray device 152 of FIG. 1. In some embodiments, the fluoroscopy images 710 may be obtained while no contrast agent is present within the patient vasculature. Such an embodiment is shown by the fluoroscopy images 710 in FIG. 7. The radiopaque portion of the intravascular device 720 is visible within the fluoroscopy image 710. The fluoroscopy images 710 may correspond to a continuous image stream of fluoroscopy images and may be obtained as the patient anatomy is exposed to a reduced dose of x-radiation. It is noted that the fluoroscopy images 710 may be acquired with the x-ray source 160 and the x-ray detector 170 positioned at any suitable angle in relation to the patient anatomy. This angle is shown by angle 790.

The intravascular device 720 may be any suitable intravascular device. As the intravascular device 720 moves through the patient vasculature, the x-ray imaging system may acquire multiple fluoroscopy images 710 showing the radiopaque portion of the intravascular device 720. In this way, each fluoroscopy image 710 shown in FIG. 7 may depict the intravascular device 720 positioned at a different location such that a processor circuit may track the position of the intravascular device 720 over time.

As the intravascular device 720 is pulled through the patient vasculature, it may acquire intravascular data 730. In an example, the intravascular data 730 shown in FIG. 7 may be IVUS images. However, the intravascular data may be any suitable data, including IVUS images, FFR data, iFR data, OCT images, intravascular photoacoustic (IVPA) images, or any other measurements or metrics relating to blood pressure, blood flow, lumen structure, or other physiological data acquired during a pullback of an intravascular device. As described with reference to FIG. 6, the intravascular data 730 associated with a particular IVUS image may include, among other data, raw intravascular data acquired by the intraluminal imaging device 102, an IVUS image, location data corresponding to a vessel wall, location data corresponding to a lumen boundary, a cross-sectional area defined by a vessel wall, a cross-sectional area defined by a lumen boundary, a plaque burden value, and an expansion score. As described with reference to FIG. 7, any of these data may be coregistered to locations along a pathway and a location within an image 711.

As the physician pulls the intravascular device 720 through the patient vasculature, each intravascular data point 730 acquired by the intravascular device 720 may be associated with a position within the patient anatomy in the fluoroscopy images 710, as indicated by the arrow 761. For example, the first IVUS image 730 shown in FIG. 7 may be associated with the first fluoroscopy image 710. The first IVUS image 730 may be an image acquired by the intravascular device 720 at a position within the vasculature, as depicted in the first fluoroscopy image 710 as shown by the intravascular device 720 within the image 710. Similarly, an additional IVUS image 730 may be associated with an additional fluoroscopy image 710 showing the intravascular device 720 at a new location within the image 710, and so on. The processor circuit may determine the locations of the intravascular device 720 within each acquired x-ray image 710 by any suitable method. For example, the processor circuit may perform various image processing techniques, such as edge identification of the radiopaque marker, pixel-by-pixel analysis to determine transition between light pixels and dark pixels, filtering, or any other suitable techniques to determine the location of the imaging device 720. In some embodiments, the processor circuit may use various artificial intelligence methods including deep learning techniques such as neural networks or any other suitable techniques to identify the locations of the imaging device 720 within the x-ray images 710.

Any suitable number of IVUS images or other intravascular data points 730 may be acquired during an intravascular device pullback and any suitable number of fluoroscopy images 710 may be obtained. In some embodiments, there may be a one-to-one ratio of fluoroscopy images 710 and intravascular data 730. In other embodiments, there may be differing numbers of fluoroscopy images 710 and/or intravascular data 730. The process of co-registering the intravascular data 730 with one or more x-ray images may include some features similar to those described in U.S. Pat. No. 7,930,014, titled, "VASCULAR IMAGE CO-REGISTRATION," and filed Jan. 11, 2006, which is hereby incorporated by reference in its entirety. The co-registration process may also include some features similar to those described in U.S. Pat. Nos. 8,290,228, 8,463,007, 8,670,603, 8,693,756, 8,781,193, 8,855,744, and 10,076,301, all of which are also hereby incorporated by reference in their entirety.

The system 100 may additionally generate a fluoroscopy-based 2D pathway 740a defined by the positions of the intravascular device 720 within the x-ray fluoroscopy images 710. The different positions of the intravascular device 720 during pullback, as shown in the fluoroscopy images 710, may define a two-dimensional pathway 740a, as shown by the arrow 760. The fluoroscopy-based 2D pathway 740a reflects the path of one or more radiopaque portions of the intravascular device 720 as it moved through the patient vasculature as observed from the angle 790 by the x-ray imaging device 152. The fluoroscopy-based 2D pathway 740a defines the path as measured by the x-ray device which acquired the fluoroscopy images 710, and therefore shows the path from the same angle 790 at which the fluoroscopy images were acquired. Stated differently, the 2D pathway 740a describes the projection of the 3D path followed by the device onto the imaging plane at the imaging angle 790. In some embodiments, the pathway 740a may be determined by an average of the detected locations of the intravascular device 720 in the fluoroscopy images 710. For example, the pathway 740a may not coincide exactly with the guidewire in any fluoroscopy image 710 selected for presentation.

As shown by the arrow 762, because the two-dimensional path 740a is generated based on the fluoroscopy images 710, each position along the two-dimensional path 740a may be associated with one or more fluoroscopy images 710. As an example, at a location 741 along the path 740a, the first fluoroscopy image 710 may depict the intravascular device 720 at that same position 741. In addition, because a correspondence was also established between the fluoroscopy images 710 and the intravascular data 730 as shown by the arrow 761, intravascular data 730, such as the first IVUS image shown, may also be associated with the location 741 along the path 740a as shown by the arrow 763.

Finally, a path 740b may be overlaid onto a contrast x-ray image 711. The path 740b may be the same as the path 740a. The path 740b may be positioned within the image 711 such that it aligns with the contrast vessel 742 imaged. A user of the system may position the path 740b or a processor circuit may automatically determine a position of the path 740b within the image 711. In some embodiments, the image 711 may alternatively be a no contrast image (e.g., one of the fluoroscopic images 710 in the fluoroscopic image stream). In such an embodiment, the pathway 740b may be overlaid over the image 711 so as to align with an observed guidewire within the image 711. In embodiments in which the image 711 includes a contrast image, such as the image 711 shown in FIG. 7, the processor circuit may be configured to overlay the pathway 740b over the image 711 so as to align with a contrast filled vessel (e.g., the vessel 742) of the image 711. In some embodiments, the image 711 may be acquired by the x-ray imaging system at the same angle 790 as the images 710, as shown in FIG. 7. This may ensure that the pathway 740*b* may align with the imaged vessel shown in the image 711 as closely as possible.

As described, any location along the path 740*b* displayed on the image 711 may be associated with IVUS data such as an IVUS image 730 and/or an expansion score 605, as shown by the arrow 764. For example, IVUS image 730 shown in FIG. 7 may be acquired simultaneously with the fluoroscopy image 710 shown and the two may be associated with each other as shown by the arrow 761. The fluoroscopy image 710 may then indicate the location of the intravascular device 720 along the path 740*b*, as shown by the arrow 762, thus associating the IVUS image 730 and any accompanying data with the location 741 along the path 740*b* as shown by the arrow 763. Finally, the IVUS image 730 may be associated with the location within the image 711 at which it was acquired by overlaying the path 740*b* with associated data on the contrast x-ray image 711. The pathway 740*b* itself may or may not be displayed on the image 711.

In the illustrated embodiment of FIG. 7, the co-registered IVUS images are associated with one of the fluoroscopic images obtained without contrast such that that the position at which the IVUS images are obtained is known relative to locations along the guidewire. In other embodiments, the co-registered IVUS images are associated with an x-ray image obtained with contrast (in which the vessel is visible) such that that the position at which the IVUS images are obtained is known relative to locations along the vessel.

Figure 8:
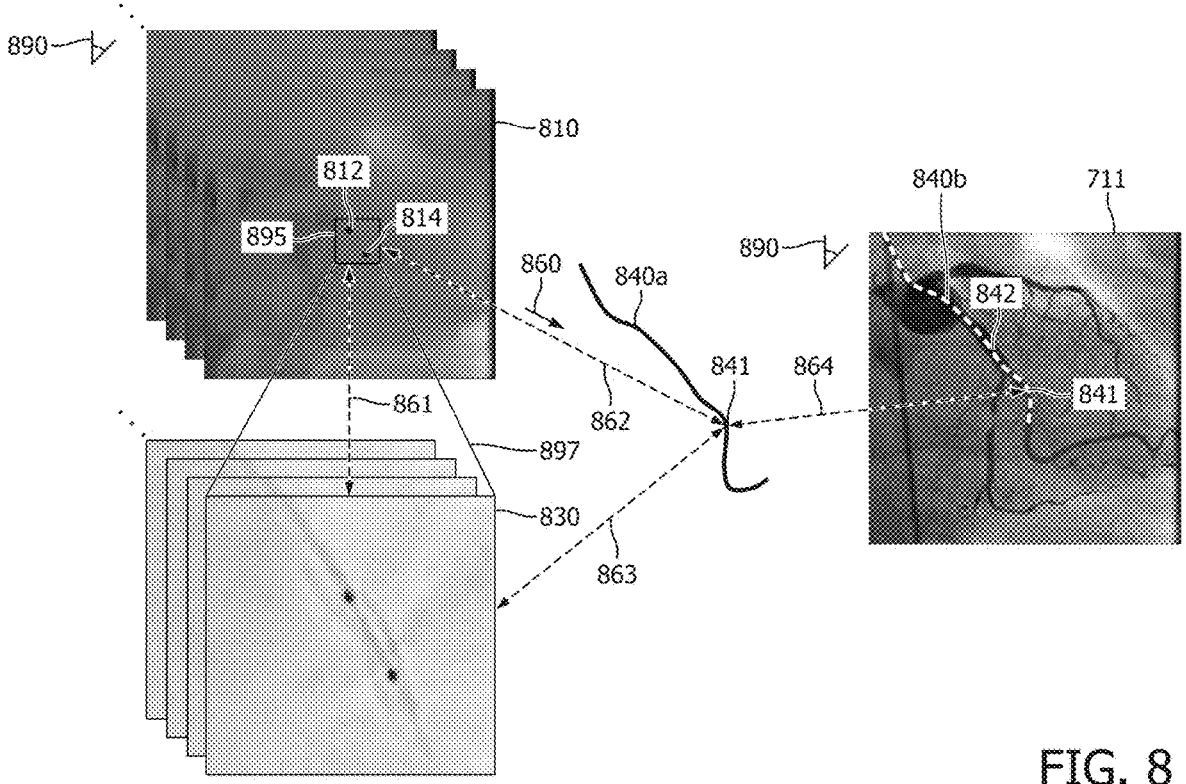
FIG. 8 is a diagrammatic view of a relationship between x-ray fluoroscopy images, a stent boosted image, and a path defined by the motion of an intravascular treatment device, according to aspects of the present disclosure.

FIG. 8 is a diagrammatic view of a relationship between x-ray fluoroscopy images 810, a stent boosted image 830, and a path 840*a* defined by the motion of an intravascular treatment device, according to aspects of the present disclosure. Aspects of the diagrammatic view of FIG. 8 may illustrate a method of coregistering one or more stent-enhanced images 830 with corresponding locations on one or more no contrast images 810 of the same region of a patient's anatomy. It is noted that any suitable number of stent-enhanced images 830 may be coregistered to locations along a pathway (e.g., the pathway 840*a*) and/or locations within x-ray fluoroscopy images 810. However, for purposes of describing FIG. 8, the coregistration of a single stent-enhanced image 830 is described. Any of the principles described, however, may apply to the coregistration of multiple stent-enhanced images 830. The methods described with reference to FIG. 8 may be employed by the processor circuit 510 to coregister a stent-enhanced image 830 with locations along a guidewire within the imaged vessel, a pathway such as the pathway 840*a*, or locations along the vessel itself in embodiments in which a contrast agent is introduced to the imaged vessel. Steps of the present disclosure may additionally include positioning and expanding a stent and obtaining a stent boosted image. Stent-enhanced images may also be referred to as stent-boosted x-ray images, magnified stent x-ray images, enhanced stent deployment x-ray images, or any other suitable term. Examples of stent-enhanced images include StentBoost images available from Koninklijke Philips N.V., ClearStent images available from Siemens, StentViz/PCI Assist images available from GE Healthcare.

The patient anatomy may be imaged with an x-ray device while a physician performs a treatment procedure (e.g., deployment of a stent). As the treatment device moves through a blood vessel of the anatomy, the x-ray device may acquire x-ray fluoroscopy images 810. The x-ray device used to obtain the fluoroscopy images 810 may be substantially similar to the x-ray device 152 of FIG. 1. In some embodiments, the fluoroscopy images 810 may be obtained while no contrast agent is present within the patient vasculature. Such an embodiment may be shown by the fluoroscopy images 810 in FIG. 8. Radiopaque portions of the treatment device may be visible within the fluoroscopy image 810. For example, a proximal radiopaque marker 812 is shown within the image 810. A distal radiopaque marker 814 is also shown. These radiopaque markers 812 and 814 may be markers positioned on a delivery device for the stent (e.g., radiopaque markers of the delivery balloon of the stent delivery catheter). In addition, radiopaque struts of the stent 1158 may also be visible within any of the images 830. The stent struts may identify for an operator of the system 100 the location of a deployed stent as well as the degree of expansion of the stent. The fluoroscopy images 810 may correspond to a continuous image stream of fluoroscopy images and may be obtained as the patient anatomy is exposed to a reduced dose of x-radiation. It is noted that the fluoroscopy images 810 may be acquired with the x-ray source 160 and the x-ray detector 170 positioned at any suitable angle in relation to the patient anatomy. This angle is shown by angle 890. In some embodiments, the angle 890 may be the same angle or a substantially similar angle as the angle 790.

The treatment device deployed may be any suitable treatment device, such as a stent. As the treatment device moves through the patient vasculature, the x-ray imaging system may acquire multiple fluoroscopy images 810 showing the radiopaque portions of a delivery device of the stent. In this way, each fluoroscopy image 810 shown in FIG. 8 may depict the delivery device and/or stent positioned at a different location such that a processor circuit may track the position of the delivery device and/or stent over time.

As the physician positions the stent within the patient vasculature, each position of the radiopaque markers 812 and 814 may be observed in the fluoroscopy images 810, as indicated by the arrow 861. The processor circuit may determine the locations of the stent within each acquired x-ray image 810 by any suitable method. For example, the processor circuit may perform various image processing techniques, such as edge identification of the radiopaque markers, pixel-by-pixel analysis to determine transition between light pixels and dark pixels, filtering, or any other suitable techniques to determine the location of the treatment device. In some embodiments, the processor circuit may use various artificial intelligence methods including deep learning techniques such as neural networks or any other suitable techniques to identify the locations of the stent within the x-ray images 810.

In some aspects, the fluoroscopy image 810*d* may be an x-ray fluoroscopy image obtained after the stent has been moved to the intended location within the vessel and expanded. The additional images 810*a*, 810*b*, and 810*c* may be fluoroscopy images obtained prior to the time at which the image 810*d* was imaged. For example, any of the images 810*a*, 810*b*, or 810*c*, as well as any other additional images within the continuous image stream may depict the radiopaque portions 812 and 814 of the device at different locations proximal to the locations of the portions 812 and 814 as seen in the image 810*d*. These images 810*a*, 810*b*, and 810*c* may have been obtained as the stent was moved through the body lumen prior to stent deployment.

The stent-enhanced image 830 shown may be a stent-enhanced image acquired after the stent was positioned and expanded. In some aspects, the image 830 shown may correspond to the fluoroscopy image 810*d*. For example, the image 830 may have been generated based on the image 810*d*. In that regard, the stent-enhanced image 830 may be a portion of the fluoroscopy image 810*d*, as shown by the box 895 and lines 896 and 897. Similarly, as shown by the arrows 862 and 863, the stent-enhanced image 830 and the fluoroscopy image 810*d* may be associated with the location 841 along the pathway 840*a*.

A stent-enhanced image may be a region within an extraluminal image, such as an x-ray image, depicting a stent that is image-processed. For example, the processing of a stent-enhanced image may differ from the processing of other x-ray images in order to emphasize the appearance of the stent details (e.g., stent struts, geometry, etc.). In some embodiments, the x-ray image may be obtained using additional x-ray exposure in order to allow for the additional image processing within the region to generate the stent-enhanced image as well as to increase the image's intrinsic quality. A stent-enhanced image may increase the visibility of a stent being inserted, or already inserted, into a patient's vessel. A stent-enhanced image may be generated based on radiopaque markers of a treatment device such as a delivery device (e.g., a delivery balloon), or radiopaque features of the stent. A stent-enhanced image may include a still image of the stent with enhanced edges as well as a region around the stent. A stent-enhanced image may enhance visibility of stent struts within the image.

In one instance, a stent-enhanced image may be generated based on a StentBoost technique based on the automatic detection of two radiopaque markers in different frames of a plurality of extraluminal images. The extraluminal images may include images of different exposure. The radiopaque markers may be positioned on a balloon catheter used for stent placement or on the stent. In some aspects, stent placement may correspond to a longitudinal position of the stent as well as expansion of the stent. After expansion of the stent at the desired location within the vessel, the delivery catheter may be maintained in a stable position inside the expanded stent. With the delivery catheter and stent in this position, an exposure passageway may be performed using the cardiac x-ray system. The catheter may then be removed and the data obtained from the exposure passageway may be processed by a processor circuit to generate a stent-enhanced image. Aspects of generating stent-enhanced image as well as aspects of stent-enhanced images themselves may include any features similar to those described in DE Patent Application No. DE102007023719A1, filed May 22, 2007 and U.S. Pat. No. 79,410,000, titled, "Method for Producing an Image and System for Producing an Image," filed May 11, 2007, both of which are hereby incorporated by reference in their entirety.

The system 100 may additionally generate a fluoroscopy-based 2D pathway 840*a* defined by the positions of the treatment device within the x-ray fluoroscopy images 810. The different positions of the treatment device during positioning, as shown in the fluoroscopy images 810, may define a two-dimensional pathway 840*a*, as shown by the arrow 860. The fluoroscopy-based 2D pathway 840*a* reflects the path of the radiopaque portions of the treatment device (e.g., the markers 812 and 814) as it moved through the patient vasculature as observed from the angle 890 by the x-ray imaging device 152. The fluoroscopy-based 2D pathway 840*a* defines the path as measured by the x-ray device which acquired the fluoroscopy images 810, and therefore shows the path from the same angle 890 at which the fluoroscopy images were acquired. Stated differently, the 2D pathway

840*a* describes the projection of the 3D path followed by the device onto the imaging plane at the imaging angle 890. In some embodiments, the pathway 840*a* may be determined by an average of the detected locations of the treatment device in the fluoroscopy images 810. For example, the pathway 840*a* may not coincide exactly with the guidewire in any fluoroscopy image 810 selected for presentation.

As shown by the arrow 862, because the two-dimensional path 840*a* is generated based on the fluoroscopy images 810, each position along the two-dimensional path 840*a* may be associated with one or more fluoroscopy images 810. As an example, at a location 841 along the path 840*a*, the fluoroscopy image 810*d* may depict the treatment device at that same position 841.

Finally, a path 840*b* generated based on the locations of the treatment device within the fluoroscopy images 810 may be overlaid onto the contrast x-ray image 711. The path 840*b* may be the same as the path 840*a*. The contrast image 711 may be the same contrast image 711 shown in FIG. 7, to which IVUS data 730 was coregistered. In embodiments in which the image 711 includes a contrast image, such as the image 711 shown in FIG. 8, the processor circuit may be configured to overlay the pathway 840*b* over the image 711 so as to align with the contrast filled vessel 842 imaged shown in the image 711. The user or the processor circuit 510 may position the path 840*b* within the image 711. In some embodiments, the image 711 may be acquired by the x-ray imaging system at the same angle 890 as the images 810, as shown in FIG. 8. This may ensure that the pathway 840*b* may align with the imaged vessel shown in image 711 as closely as possible.

As described, the location 841 along the path 840*b* displayed on the image 711 may be associated with the stent-enhanced image 830, as shown by the arrow 864. For example, the stent-enhanced image 830 shown in FIG. 8 may be acquired simultaneously with the fluoroscopy image 810*d* shown and the two may be associated with each other as shown by the arrow 861. The fluoroscopy image 810*d* may then indicate the location of the treatment device along the path 840*b*, as shown by the arrow 862, thus associating the stent-enhanced image 830 with the location 841 along the path 840*b* as shown by the arrow 863. Finally, the stent-enhanced image 830 may be associated with the location within the image 711 at which it was acquired by overlaying the path 840*b* with associated data on the contrast x-ray image 711. The pathway 840*b* itself may or may not be displayed on the image 711.

In the illustrated embodiment of FIG. 8, the co-registered stent-enhanced image 830 is associated with the fluoroscopic image 810*d* obtained without contrast such that that the position at which the image 810*d* and corresponding stent-enhanced image 830 are obtained is known relative to locations along the guidewire. In other embodiments, the co-registered stent-enhanced image 830 may be associated with an x-ray image obtained with contrast (in which the vessel is visible) such that that the position at which the stent-enhanced image was obtained is known relative to locations along the vessel.

As described with reference to FIG. 7 and FIG. 8, and as will be described in more detail with reference to FIG. 9, both the IVUS data of FIG. 7 and the stent location data of the stent-enhanced image 830 of FIG. 8 may be coregistered to the same image 711. A positional relationship between the IVUS data of FIG. 7 and the stent location data of FIG. 8 may thus be established.

Figure 9:
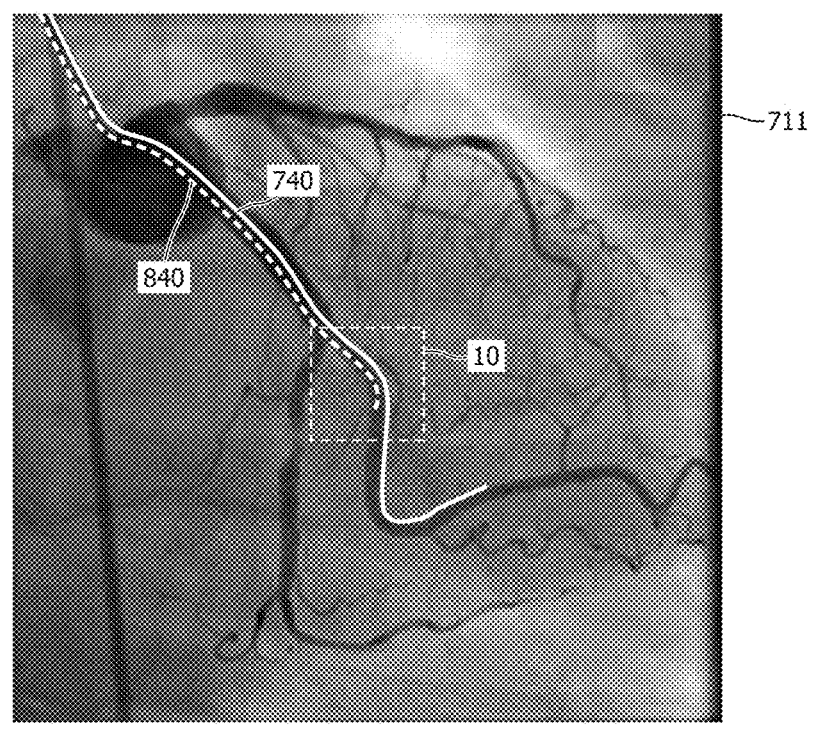
FIG. 9 is a diagrammatic view of an extraluminal image with a pathway of an intravascular imaging device and a pathway of an intravascular treatment device, according to aspects of the present disclosure.

FIG. 9 is a diagrammatic view of an extraluminal image 711 with a pathway 740 of an intravascular imaging device and a pathway 840 of an intravascular treatment device, according to aspects of the present disclosure. The pathway 840 may correspond to movement of the stent before it is expanded. In some embodiments, the image 711 shown in FIG. 9 may be the same contrast x-ray image 711 described with reference to FIG. 7 and FIG. 8. The image 711 shown in FIG. 9 may or may not be displayed to a user.

FIG. 9 includes the pathway 740 and the pathway 840. The pathway 740, as described with reference to FIG. 7, may be defined by multiple coordinates relating to the path of an intravascular imaging device during a pullback procedure. The pathway 840, as described with reference to FIG. 8, may be defined by multiple coordinates relating to the path of the stent during a stent deployment procedure. Each location along the pathway 740 may correspond to an IVUS image. Each location along the pathway 840 may correspond to the location of a stent during a deployment procedure (e.g., a stent being moved into position before the stent is expanded, with the last location of the stent along the pathway 840 corresponding to the location at which the stent is expanded). As shown in FIG. 9, the pathway 740 and/or the pathway 840 may extend along the same vessel but may correspond to different sections of the vessel. For example, the pathway 740 shown in FIG. 9 may extend in a distal direction along the imaged vessel farther than the pathway 840. This situation, shown in FIG. 9, may relate to a case in which the IVUS imaging device was positioned at a starting location at a location distal to any positions of the stent during deployment (e.g., the pathway 840). The opposite may be true in other circumstances. In some cases, the pathway 740 and the pathway 840 may be the same length or correspond to the same sections of the imaged vessel. In the example shown, any regions of the vessel corresponding to both the pathway 740 and the pathway 840 may be associated with both one or more IVUS images and location information of the stent.

As shown by the box 10, a distal region of the pathway 840 may correspond to the final location or placement of a stent after a deployment procedure is completed. The box 10 may identify a region corresponding to an enlarged portion of the image 711 described in more detail with reference to FIG. 10.

Figure 10:
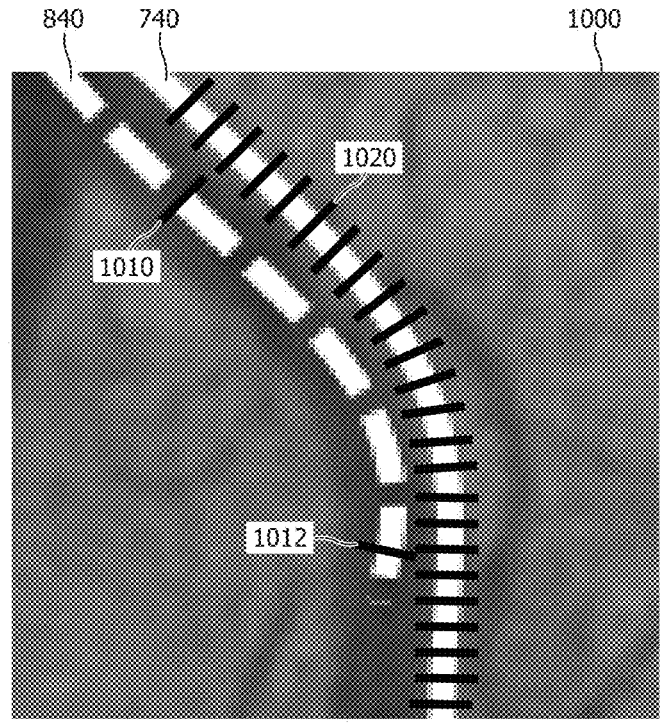
FIG. 10 is a diagrammatic view of an enlarged portion of an extraluminal image, according to aspects of the present disclosure.

FIG. 10 is a diagrammatic view of an enlarged portion 1000 of an extraluminal image, according to aspects of the present disclosure. The enlarged portion 1000 may be region of the image 711. This enlarged view 1000 may include a region of the imaged vessel as well as a region of the pathway 840 and a region of the pathway 740. As shown in FIG. 10, both the pathway 840 and the pathway 740 may include various indicators.

As an example, an indicator 1010 is shown displayed overlapping the pathway 840. This indicator 1010 may correspond to a proximal end of a stent. Specifically, referring again to FIG. 8, the indicator 1010 may indicate the location of the proximal radiopaque marker 812 of the stent. Similarly, the indicator 1012 may correspond to a distal end of the deployed stent. Specifically, the indicator 1012 may indicate the location of the distal radiopaque marker 812 of the stent. The view of the ends of the stent in the enlarged portion 1000 may correspond to the location of a stent before or after deployment. In this way, the location of the stent along the pathway 840 may be determined by the processor circuit (e.g., via an image processing algorithm) based on the distal radiopaque marker 814 and the proximal radiopaque marker 812. The processor circuit may also use these markers 812 and 814 to generate the stent-enhanced image.

A visualization of the metal struts of the expanded stent may assist a user in determining whether the stent is properly expanded.

In some embodiments, a length or distance between the proximal and distal radiopaque markers of the stent as shown by the indicators 1010 and 1012 may be known. For example, the processor circuit 510 may determine or receive the distance between the proximal and distal radiopaque markers of the stent. In some embodiments, the circuit 510 may determine this length by referring to various stored parameters of the stent stored in a memory in communication with the circuit. In other embodiments, the circuit 510 may receive this length measurement as a user input. In some embodiments, this length may be associated with another unit of measure of the image 1000 and/or the image 711 described previously. For example, the length between the radiopaque markers may be stored as a distance along the pathway 840 in pixels of the image, or by any other unit. This length may be used by the processor circuit 510 as a reference unit to determine other lengths or distances within any of the received extraluminal images described herein.

Also shown in FIG. 10 are multiple indicators 1020. In some embodiments, the indicators 1020 may identify the locations along the pathway 740 at which IVUS images were received. For example, each indicator 1020 may correspond to a single IVUS image received. In some embodiments, an indicator 1020 may correspond to multiple IVUS images. The indicators 1020 may be uniformly spaced from each other as shown or may be spaced according to any other pattern depending on the rate, whether constant or variable, at which the IVUS device 102 was pulled through the vessel.

As shown in FIG. 10, because the positions of each obtained IVUS image are known and may be displayed overlaid over the pathway 740 and because the locations of the distal and proximal radiopaque markers of the stent are known along the path 840, the positional relationships between the indicators 1020, 1010, and 1012 may be established. In this way, a user may identify an IVUS image acquired closest to, for example, the proximal or distal radiopaque marker of the deployed stent or any position therebetween, including e.g., any portions of the stent which may be under expanded. As explained hereafter, due to this positional relationship, various acquired stent-enhanced images may also be correlated with IVUS images acquired at or near these locations.

Figure 11:
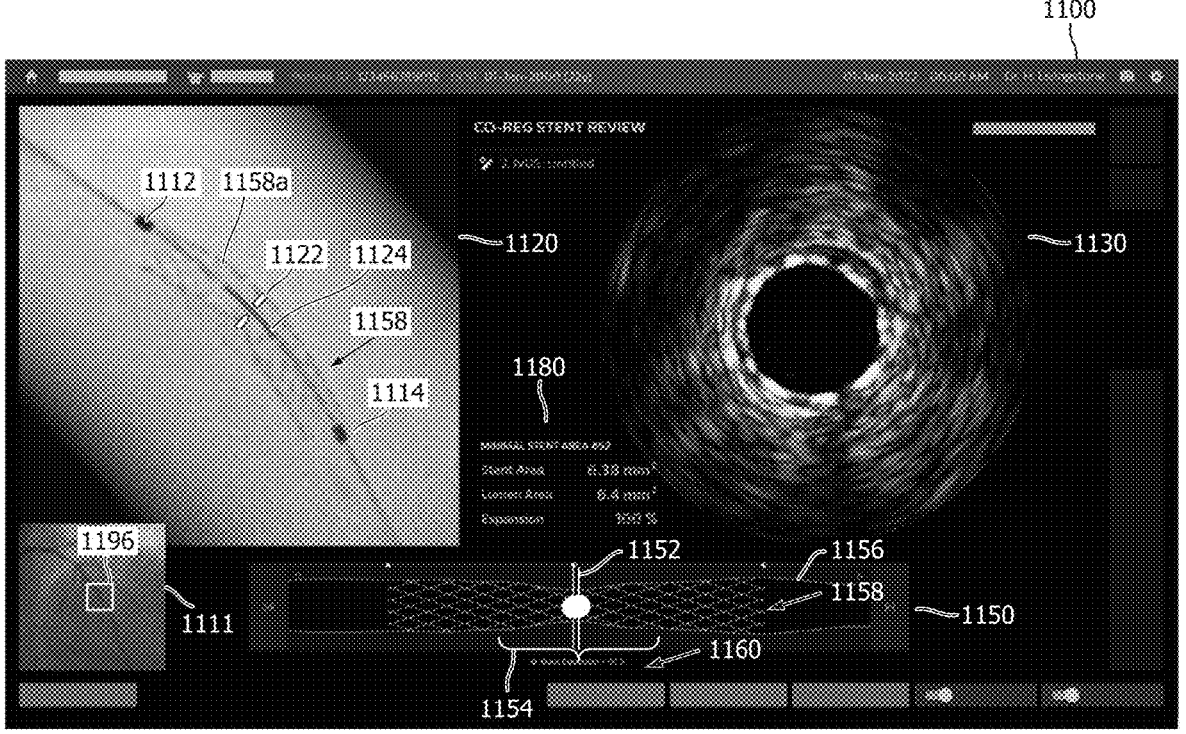
FIG. 11 is a diagrammatic view of a graphical user interface with a stent-enhanced image, an IVUS image, and a longitudinal view of a vessel, according to aspects of the present disclosure.

FIG. 11 is a diagrammatic view of a graphical user interface 1100 with a stent-enhanced image 1120, an IVUS image 1130, and a longitudinal view 1150 of a vessel, according to aspects of the present disclosure. The graphical user interface 1100 may additionally include a contrast x-ray image 1111.

The IVUS image 1130 shown in FIG. 11 may be any of the IVUS images received during an IVUS imaging pullback procedure. The IVUS image 1130 may include a depiction of a vessel wall, a lumen boundary, a stent wall, or any other feature. In some embodiments, the IVUS image 1130 may additionally display various graphical elements used to identify or highlight features of the image 1130. For example, any suitable graphical elements may be overlaid over the image 1130 to identify a vessel wall, a lumen boundary, a stent wall, or any other features. In some aspects, the processor circuit (e.g., the processor circuit 510 of FIG. 5) may identify a stent 1158 within the image 1130 based on the presence of stent struts 1158a detected within the image 1130. For example, as shown in FIG. 11, various stent struts may be present within or around the lumen of the blood vessel. Some stent struts 1158a are identified within the image 1130, however, it is understood that additional struts 1158a may be present but not identified explicitly.

The graphical user interface 1100 may additionally display various metrics 1180. For example, the metrics 1180 may be associated with the displayed IVUS image 1130. The metrics 1180 may include a label of the IVUS image 1130. The label may include a number referring to the order at which the IVUS image 1130 was acquired in comparison to other IVUS images. The title may also include an indication of any point of interest associated with the IVUS image 1130, including, for example, that the image corresponds to a minimum stent area, a maximum stent area, a minimum lumen area, a maximum lumen area, a minimum vessel area, a maximum vessel area, a minimum stent expansion, a maximum stent expansion, a minimum plaque burden, a maximum plaque burden, or any other features of interest associated with the image 1130. In some embodiments, the metric 1180 may include a stent area metric, a lumen area metric, a vessel area metric, a plaque burden, and an expansion metric, as well as any other metrics. Aspects of calculating and displaying any of these metrics 1180 described herein may include features similar to those described in U.S. application Ser. No. 16/354,970, titled "Determination and visualization of anatomical landmarks for intraluminal lesion assessment and treatment planning," filed Mar. 15, 2019, U.S. application Ser. No. 16/520,472, titled "Intravascular imaging procedure-specific workflow guidance and associated devices, systems, and methods," filed Jul. 24, 2019, U.S. application Ser. No. 16/299,091, titled "Scoring intravascular lesions and stent deployment in medical intraluminal ultrasound imaging," filed Mar. 11, 2019, U.S. application Ser. No. 16/520,541, titled "Systems, devices, and methods for displaying multiple intraluminal images in luminal assessment with medical imaging," filed Jul. 24, 2019, each of which is hereby incorporated by reference in its entirety.

The stent-enhanced image 1120 may be the stent-enhanced image 830 described with reference to FIG. 8. In some embodiments, the stent-enhanced image 1120 may be a region of a no-contrast x-ray image depicting a stent after it is deployed. The stent-enhanced image 1120 may include depictions of the stent 1158 as well as a proximal radiopaque marker 1112, a distal radiopaque marker 1114, and the metal struts 1158a of the stent. A depiction of a guidewire may also be present in the stent-enhanced image 1120 in some embodiments. The stent-enhanced image 1120 may also include an indicator 1122. This indicator 1122 may be overlaid over a portion of a guidewire or a portion of the stent. The indicator 1122 may illustrate, for a user, the location at which the IVUS image 1130 displayed proximate to the image 1120 was acquired. In some embodiments, the stent-enhanced image 1120 may be displayed to a user automatically in response to a selection of a location along the stent 1158. For example, before the selection of a location along the stent 1158, a different extraluminal image, such as the image 1111, may be displayed in the stent-enhanced image 1120's place. However, when a cursor (e.g., the cursor 1152 and/or the cursor 1122) is moved to a region corresponding the stent 1158, the stent-enhanced image 1120, along with any coregistered data (e.g., the indicator 1124 or other data) may be displayed. In this way, a user may browse through multiple IVUS images and/or locations along the vessel. When browsing IVUS frames belonging to a stent, the stent-enhanced image may be shown as a picture in picture on the IVUS review screen. Outputs of the present system may include an image on the stent boost, post stent IVUS images and/or data output correlated with the boosted image of the stent and/or an ILD.

The graphical user interface 1100 may also include one example of a longitudinal intraluminal image 1150. The longitudinal image 1150 may be referred to as in-line digital (ILD) display or intravascular longitudinal display (ILD) 1150. The IVUS images acquired during an intravascular ultrasound imaging procedure, such as during an IVUS pullback, may be used to create the ILD 1150. In that regard, an IVUS image is a tomographic or radial cross-sectional view of the blood vessel. The ILD 1150 provides a longitudinal cross-sectional view of the blood vessel. The ILD 1150 can be a stack of the IVUS images acquired at various positions along the vessel, such that the longitudinal view of the ILD 1150 is perpendicular to the radial cross-sectional view of the IVUS images. In such an embodiment, the ILD 1150 may show the physical length of the vessel, whereas an individual IVUS image is a single radial cross-sectional image at a given location along the length. The physical length of the vessel, including relative lengths between various positions along the ILD may be determined based on a distance calibration achieved through co-registration. In other embodiments, a length of the ILD may correspond to the time at which IVUS images used to generate the ILD were received. In another embodiment, the ILD 1150 may be a stack of the IVUS images acquired overtime during the imaging procedure and the length of the ILD 1150 may represent time or duration of the imaging procedure. The ILD 1150 may be generated and displayed in real time or near real time during the pullback procedure. As each additional IVUS image is acquired, it may be added to the ILD 1150. For example, at a point in time during the pullback procedure, the ILD 1150 shown in FIG. 9 may be partially complete. In some embodiments, the processor circuit may generate an illustration of a longitudinal view of the vessel being imaged based on the received IVUS images. For example, rather than displaying actual vessel image data, the illustration may be a stylized version of the vessel, with e.g., continuous lines showing the lumen border and vessel border. As shown in FIG. 11, the ILD 1150 may represent a stylized ILD shown the lumen border 1156 extending as continuous lines across the ILD 1150. The location of the lumen borders 1156 may be positioned symmetrically around a center axis and may be positioned according to the luminal diameter calculated in each corresponding IVUS image.

A stylized version of the stent 1158 is also shown overlaid over the stylized ILD 1150. A distal end of the stylized version of the stent 1158 shown in the ILD 1150 may correspond to the location of the distal radiopaque marker 1114. A proximal end of the stylized version of the stent 1158 shown in the ILD 1150 may correspond to the location of the proximal radiopaque marker 1112.

Additionally, a region 1154 may be displayed on the ILD 1150. In some embodiments, the expansion score of each IVUS image received may be calculated for all IVUS images depicting a stent wall boundary. A threshold expansion score may also be determined. For any location along the ILD 1150 corresponding to an expansion score below the threshold expansion score, the depiction of the stent 1158 at that location along the ILD 1150 may be altered. For example, the stent 1158 may be colored red or any other color at any location corresponding to an expansion score below the threshold. Alternatively, regions of the stent 1158 corresponding to an expansion score below the threshold may be visually differentiated in any other way, including varying patterns, shading, indicators, or any other visual characteristics. As an example, the region 1154 may correspond to a region of the ILD 1150 with an expansion score lower than the threshold.

The region 1154 may correspond to locations along the ILD and/or IVUS images corresponding to an expansion score which does not satisfy a threshold expansion score. An indicator may identify the region 1154. In some embodiments, an indicator may identify regions of the ILD other than the region 1154 (e.g., regions corresponding to the expansion score satisfying the threshold expansion score).

In addition, an indicator 1152 may be displayed overlaid over the ILD 1150. This indicator 1152 may identify the location at which the IVUS image 1130 was obtained. In this way, the indicator 1152 may be similar to the indicator 1122 of the stent-enhanced image 1120. In some embodiments, the processor circuit 510 may be configured to receive an input from a user moving either the indicator 1122 or the indicator 1152. As either is selected and moved, the circuit 510 may be configured to move the unselected to a corresponding location. In addition, the IVUS image corresponding to the new location may be displayed on the interface 1100.

An additional expansion score 1160 may be provided in relation to the ILD 1150. In some embodiments, this expansion score 1160 may be a threshold expansion score. In some aspects, this score 1160 may be changed by the user. In other embodiments, the expansion score 1160 may be an average expansion score of a region of the ILD 1150, such as an average expansion score of the region 1154, the region corresponding to the stent 1158, or any other region.

Additionally shown in the stent-enhanced image 1120 is an indicator 1124. In some embodiments, the indicator 1124 may correspond to the region 1154 of the ILD 1150. For example, all locations along the ILD 1150 identified by the region 1154 (corresponding to a stent expansion score not satisfying a threshold) may be identified within the stent-enhanced image 1120 by the indicator 1124. The indicator 1124 may extend over all regions along the guidewire or stent 1158 corresponding to IVUS images with an expansion score below the threshold (e.g., below 90%). In some aspects, an indicator may also be overlaid over the stent-enhanced image 1120 corresponding to regions along the guidewire, stent, or body lumen with expansion scores which satisfy the threshold expansion score. In some embodiments, the information relating to underexpansion, including e.g., the indicator 1124, as well as a depiction of the stent 1158 may assist a physician in identifying "dog-boning" of the stent 1158. In some embodiments, various artificial intelligence algorithms may be used to identify whether a stent-enhanced image includes a view of a stent, such as the stent 1158, which is underexpanded or incorrectly positioned. The same or separate artificial intelligence algorithms may analyze IVUS images and/or IVUS data in conjunction with the stent-enhanced image to identify underexpansion, misplacement, or dogboning of stents as well.

The interface 1100 may also include an extraluminal image 1111 of the plurality of extraluminal images, such as an angiogram image or contrast x-ray image 1111. In some embodiments, the image 1111 may be the image to which the stent-enhanced images and IVUS data 711 were coregistered as described with reference to FIG. 7 and FIG. 8. The image 1111 may provide the user with additional context or a broader view of the patient anatomy. In some embodiments, the image 1111 may include a box 1196. This box 1196 may identify the region of the image 1111 to which the stent-enhanced image 1120 may correspond. The extraluminal image 1111 may not be a stent-enhanced image. For example, the appearance of the stent in the image 1111 may not be enhanced relative to other portions of the extraluminal image 1111.

FIG. 12 is a flow diagram of a method 1200 of generating a plaque burden indication and a longitudinal view of a vessel, according to aspects of the present disclosure. The method 1200 may describe an automatic segmentation of a vessel to detect segments of interest using co-registration of invasive physiology and x-ray images. As illustrated, the method 1200 includes a number of enumerated steps, but embodiments of the method 1200 may include additional steps before, after, or in between the enumerated steps. In some embodiments, one or more of the enumerated steps may be omitted, performed in a different order, or performed concurrently. The steps of the method 1200 can be carried out by any suitable component within the diagnostic system 100 and all steps need not be carried out by the same component. In some embodiments, one or more steps of the method 1200 can be performed by, or at the direction of, a processor circuit of the diagnostic system 100, including, e.g., the processor 560 (FIG. 5) or any other component.

At step 1210, the method 1200 includes obtaining an enhanced stent deployment extraluminal image, wherein the enhanced stent deployment extraluminal image depicts a stent positioned within a body lumen of a patient. A visual appearance of the stent in the enhanced stent deployment extraluminal image is enhanced relative to other portions of the enhanced stent deployment extraluminal image. In some aspects, step 1210 may include obtaining an enhanced stent deployment x-ray image, wherein the enhanced stent deployment x-ray image depicts a stent positioned within a body lumen of a patient and the visual appearance of the stent in the enhanced stent deployment x-ray image is enhanced relative to other portions of the enhanced stent deployment x-ray image. For the purposes of this disclosure, a processor circuit obtaining an enhanced stent deployment extraluminal image may include receiving the enhanced stent deployment extraluminal image from an extraluminal imaging system and/or from an extraluminal imaging device. Obtaining an enhanced stent deployment extraluminal image may also include processing an extraluminal image from the extraluminal imaging system and/or device and generating the enhanced stent deployment extraluminal image.

At step 1220, the method 1200 includes receiving a plurality of intraluminal images obtained by the intraluminal imaging device during the movement of the intraluminal imaging device within the body lumen. A first set of the plurality of intraluminal images obtained during the movement through the stent depicts the stent. In some aspects, the step 1220 may include receiving a plurality of IVUS images obtained by the IVUS imaging device during the movement of the IVUS imaging device within the body lumen and a first set of the plurality of IVUS images obtained during the movement through the stent depicts the stent. In some aspects, the method 1200 may further include receiving a plurality of x-ray images obtained by an x-ray imaging device. The plurality of intraluminal images or IVUS images described herein may include the first set of images obtained during movement of the imaging device through the stent as well as a images, including, for example, a second set of images obtained during movement of the imaging device through regions of the body lumen without a stent. As an example, a distal portion of the region of a vessel imaged by the intraluminal imaging device may correspond to a region of the vessel which does not correspond to a stent. A proximal portion also may not correspond to a stent. A region between the distal and proximal regions may correspond to a stent. In other words, a stent may be deployed at the middle region.

At step 1230, the method 1200 includes co-registering the plurality of intraluminal images to corresponding locations within the enhanced stent deployment extraluminal image. In some aspects, the step 1230 may include co-registering the plurality of IVUS images to corresponding locations within the enhanced stent deployment x-ray image. In some aspects, the method 1200 may further include generating a longitudinal view of the body lumen based on the plurality of IVUS images.

At step 1240, the method 1200 includes outputting, to a display in communication with the processor circuit, a screen display including the enhanced stent deployment extraluminal image and an intraluminal image of the first set of the plurality of intraluminal images. In some aspects, step 1240 may include outputting, to a display in communication with the processor circuit, a screen display including the enhanced stent deployment x-ray image, an intraluminal image of the first set of the plurality of IVUS images, the longitudinal view, and an x-ray image of the plurality of x-ray images.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A system, comprising:
a processor circuit configured for communication with an extraluminal imaging device and an intraluminal imaging device, wherein the processor circuit is configured to:
obtain an enhanced stent deployment extraluminal image, wherein the enhanced stent deployment extraluminal image depicts a stent positioned within a body lumen of a patient, wherein a visual appearance of the stent in the enhanced stent deployment extraluminal image is enhanced relative to other portions of the enhanced stent deployment extraluminal image;
receive a plurality of intraluminal images obtained by the intraluminal imaging device during the movement of the intraluminal imaging device within the body lumen, wherein a first set of the plurality of intraluminal images obtained during the movement through the stent depicts the stent, wherein the first set of the plurality of intraluminal images span multiple locations between a proximal end and a distal end of the stent;
co-register the plurality of intraluminal images to a plurality of corresponding locations within the enhanced stent deployment extraluminal image; and
output, to a display in communication with the processor circuit, a screen display comprising:

the enhanced stent deployment extraluminal image;
an intraluminal image area showing a first intraluminal image of the first set of the plurality of intraluminal images; and
an intraluminal image location marker in the enhanced stent deployment extraluminal image, wherein the intraluminal image location marker is positioned at a first location of the multiple locations and over the stent in the enhanced stent deployment extraluminal image, wherein the first intraluminal image depicts the first location,
wherein the intraluminal image location marker is configured to be moved by a user to the multiple locations, and
wherein the intraluminal image area is configured to show other intraluminal images of the first set of the plurality of intraluminal images in response to the intraluminal image location marker being moved to the multiple locations.

2. The system of claim 1, wherein the processor circuit is configured to provide the enhanced stent deployment extraluminal image in the screen display, in response to automatically identifying a stent within the intraluminal image.

3. The system of claim 1, wherein the processor circuit is further configured to determine an expansion score for one or more of the plurality of intraluminal images.

4. The system of claim 3, wherein the processor circuit is configured to automatically identify the proximal end of the stent or the distal end of the stent within one or more of the plurality of intraluminal images.

5. The system of claim 3, wherein the processor circuit is configured to compare the expansion score of the one or more intraluminal images with a threshold expansion score.

6. The system of claim 5, wherein the processor circuit is configured to identify a second set of the plurality of intraluminal images corresponding to the expansion score exceeding the threshold expansion score.

7. The system of claim 6, wherein the screen display comprises an indicator identifying one or more locations within the stent deployment extraluminal image corresponding to the expansion score exceeding the threshold expansion score.

8. The system of claim 1,
wherein the processor circuit is further configured to receive a plurality of extraluminal images,
wherein the screen display further comprises an extraluminal image of the plurality of extraluminal images.

9. The system of claim 8,
wherein the extraluminal imaging device comprises an x-ray imaging device,
wherein the plurality of extraluminal images comprises an x-ray image, and
wherein the enhanced stent deployment extraluminal image comprises an enhanced stent deployment x-ray image.

10. The system of claim 1, wherein the screen display further comprises a longitudinal view of the body lumen including the stent.

11. The system of claim 10, wherein the screen display comprises an indicator of a region of the stent in the longitudinal view corresponding to an expansion score that does not exceed a threshold expansion score.

12. The system of claim 1, wherein a length of body lumen depicted in the enhanced stent deployment extraluminal image comprises only a portion of the body lumen including the stent.

13. The system of claim 1, wherein intraluminal imaging device comprises an intra-vascular imaging catheter, wherein the body lumen comprises a blood vessel, and wherein the plurality of intraluminal images comprises a plurality of intravascular images.

14. The system of claim 13, wherein the intravascular imaging catheter is configured for intravascular ultrasound (IVUS), wherein the plurality of intravascular images comprises a plurality of IVUS images.

15. The system of claim 1, wherein the stent depicted in the enhanced stent deployment extraluminal image and in the first set of the plurality of intraluminal images is the same.

16. A method, comprising:

obtaining an enhanced stent deployment extraluminal image, wherein the enhanced stent deployment extralu-minal image depicts a stent positioned within a body lumen of a patient, wherein a visual appearance of the stent in the enhanced stent deployment extraluminal image is enhanced relative to other portions of the enhanced stent deployment extraluminal image;

receiving a plurality of intraluminal images obtained by an intraluminal imaging device during the movement of the intraluminal imaging device within the body lumen, wherein a first set of the plurality of intraluminal images obtained during the movement through the stent depicts the stent, wherein the first set of the plurality of intraluminal images span multiple locations between a proximal end and a distal end of the stent;

co-registering the plurality of intraluminal images to a plurality of corresponding locations within the enhanced stent deployment extraluminal image; and outputting, to a display in communication with the pro-cessor circuit, a screen display comprising:

the enhanced stent deployment extraluminal image;

an intraluminal image area showing a first intraluminal image of the first set of the plurality of intraluminal images; and an intraluminal image location marker in the enhanced stent deployment extraluminal image, wherein the intraluminal image location marker is positioned at a first location of the multiple locations and over the stent in the enhanced stent deployment extraluminal image, wherein the first intraluminal image depicts the first location, wherein the intraluminal image location marker is mov-able by a user to the multiple locations, and wherein the intraluminal image area shows other intralu-minal images of the first set of the plurality of intralu-minal images in response to the intraluminal image location marker being moved to the multiple locations.

* * * * *